United States Patent
Troost et al.

(10) Patent No.: US 10,226,492 B2
(45) Date of Patent: Mar. 12, 2019

(54) PROBIOTIC AND NEW BIOMARKER

(71) Applicant: DSM IP ASSETS B.V., Heerlen (NL)

(72) Inventors: Frederik Jan Troost, Maastricht (NL); Zlatan Mujagic, Stein (NL); Maria Margaretha Faas, Groningen (NL); Paulus De Vos, Slochteren (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/529,079

(22) PCT Filed: Nov. 25, 2015

(86) PCT No.: PCT/EP2015/077642
§ 371 (c)(1),
(2) Date: May 23, 2017

(87) PCT Pub. No.: WO2016/083450
PCT Pub. Date: Jun. 2, 2016

(65) Prior Publication Data
US 2017/0258858 A1     Sep. 14, 2017

(30) Foreign Application Priority Data

Nov. 25, 2014  (EP) .................................. 14194725
Nov. 25, 2014  (EP) .................................. 14194729

(51) Int. Cl.
| | | |
|---|---|---|
| *C12N 1/20* | (2006.01) | |
| *A61K 35/747* | (2015.01) | |
| *A23L 33/135* | (2016.01) | |
| *C12N 5/078* | (2010.01) | |
| *C12R 1/25* | (2006.01) | |
| *G01N 33/50* | (2006.01) | |

(52) U.S. Cl.
CPC .......... *A61K 35/747* (2013.01); *A23L 33/135* (2016.08); *C12N 1/20* (2013.01); *C12N 5/0634* (2013.01); *C12R 1/25* (2013.01); *G01N 33/5047* (2013.01); *A23V 2002/00* (2013.01); *A23Y 2220/67* (2013.01)

(58) Field of Classification Search
CPC ....... A23L 33/135; A61K 35/747; C12N 1/20; C12N 5/0634
See application file for complete search history.

(56) References Cited

U.S. PATENT DOCUMENTS

| | | |
|---|---|---|
| 2006/0257384 A1 | 11/2006 | Molin et al. |
| 2014/0335066 A1 | 11/2014 | Mikelsaar et al. |
| 2015/0240200 A1 | 8/2015 | Tsai et al. |

FOREIGN PATENT DOCUMENTS

| | | |
|---|---|---|
| CN | 102747012 A | 10/2012 |
| FR | 2848115 A1 | 6/2004 |
| WO | 2009/035330 A1 | 3/2009 |
| WO | 2011/092261 A1 | 8/2011 |
| WO | 2014/184644 A1 | 11/2014 |

OTHER PUBLICATIONS

Zhang, Zhuo-Yang et al., "Complete Genome Sequence of Lactobacillus plantarum JDM1", Journal of Bacteriology, American Society for Microbiology, Aug. 1, 2009, pp. 5020-5021, vol. 191, No. 15.
Kleerebezem, Michiel et al., "Complete genome sequence of Lactobacillus plantarum WCFS1", Proceedings of the National Academy of Sciences, National Academy of Sciences, Feb. 18, 2003, pp. 1990-1995, vol. 100, No. 4.
International Search Report of International Patent Application No. PCT/EP2015/07642 dated May 24, 2016.

*Primary Examiner* — Padmavathi Baskar
(74) *Attorney, Agent, or Firm* — McBee Moore Woodward & Vanik IP, LLC; Susan McBee; Chester Moore

(57) ABSTRACT

The present invention relates to a new probiotic with immune modulating properties and to a new biomarker.

Figure 1A:
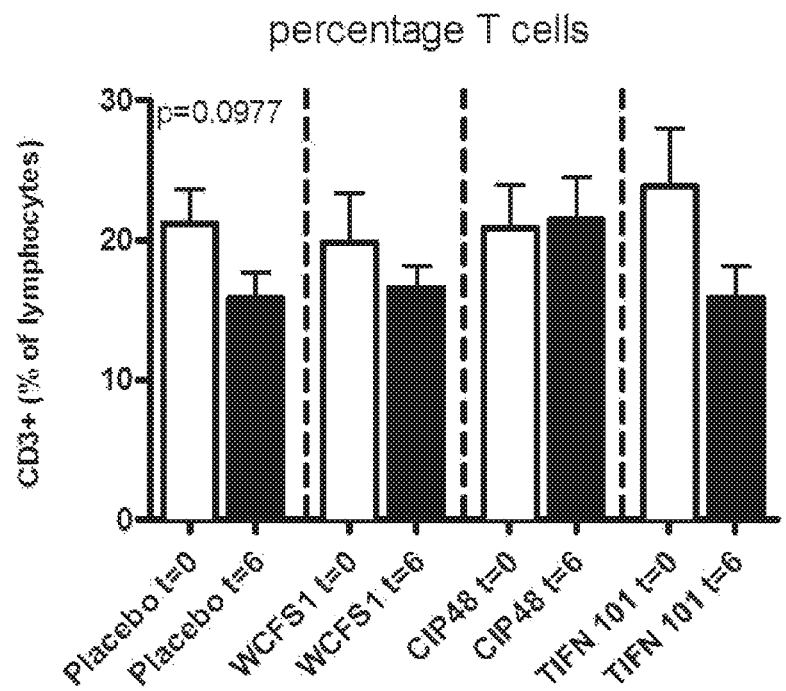
Figure 1B:
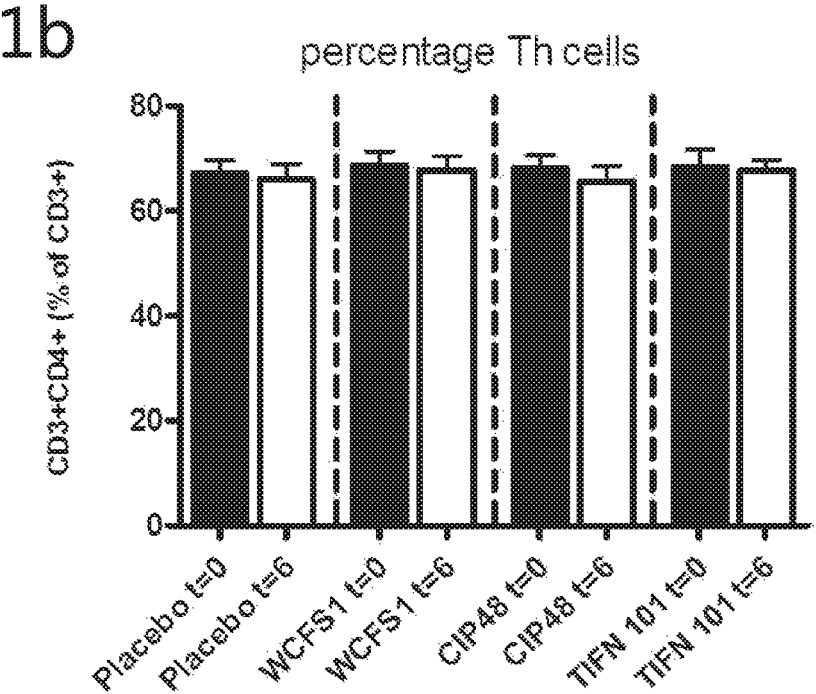
Figure 1C:
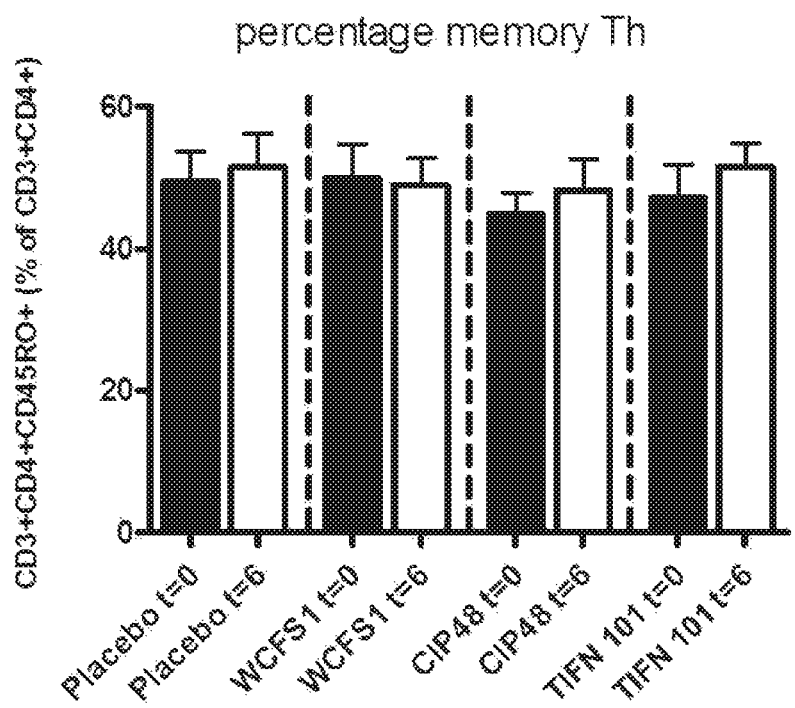
Figure 1D:
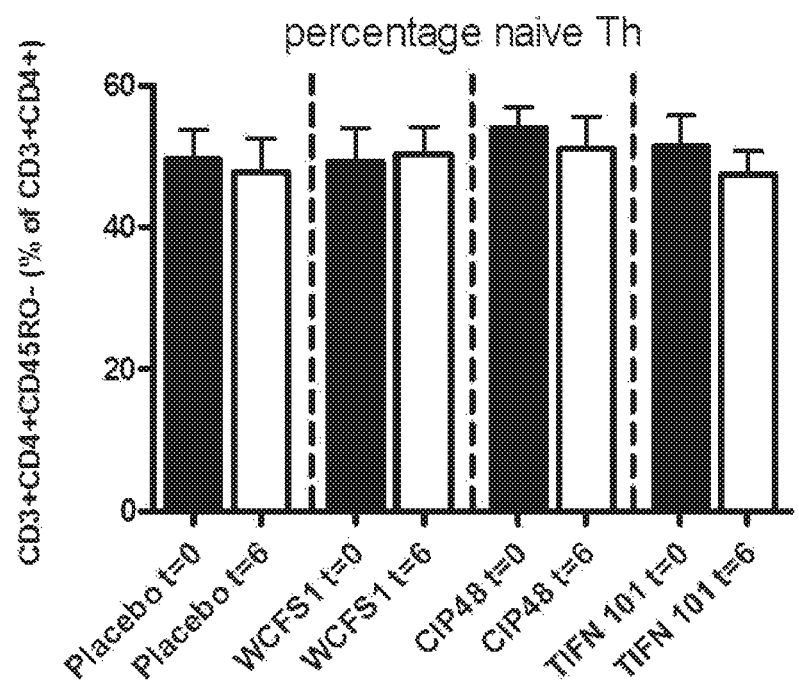
Figure 1E:
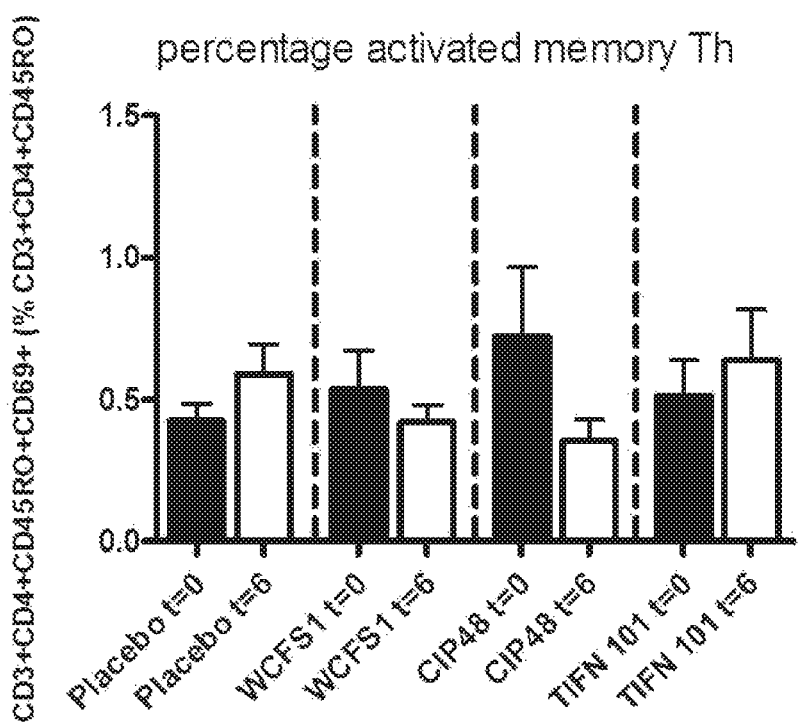
Figure 1F:
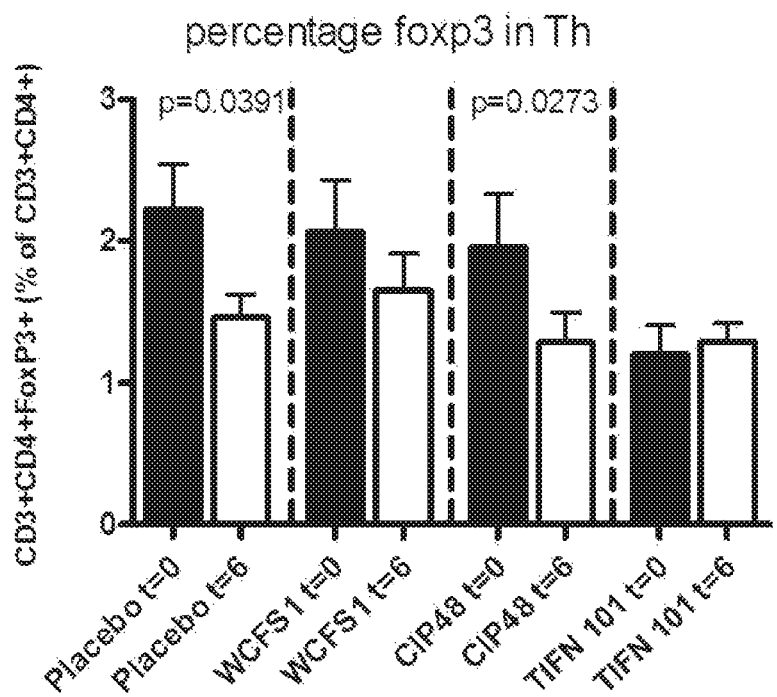
Figure 1G:
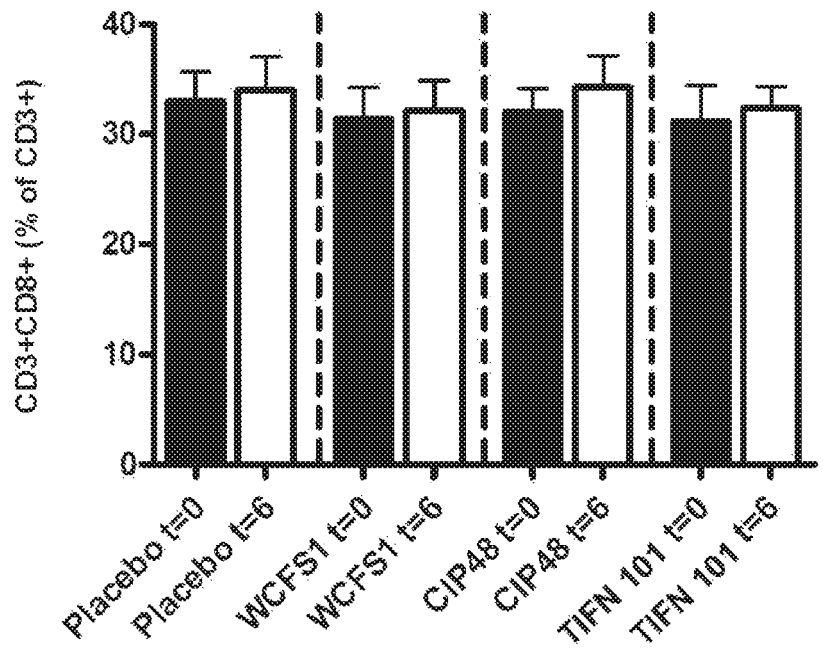
Figure 1H:
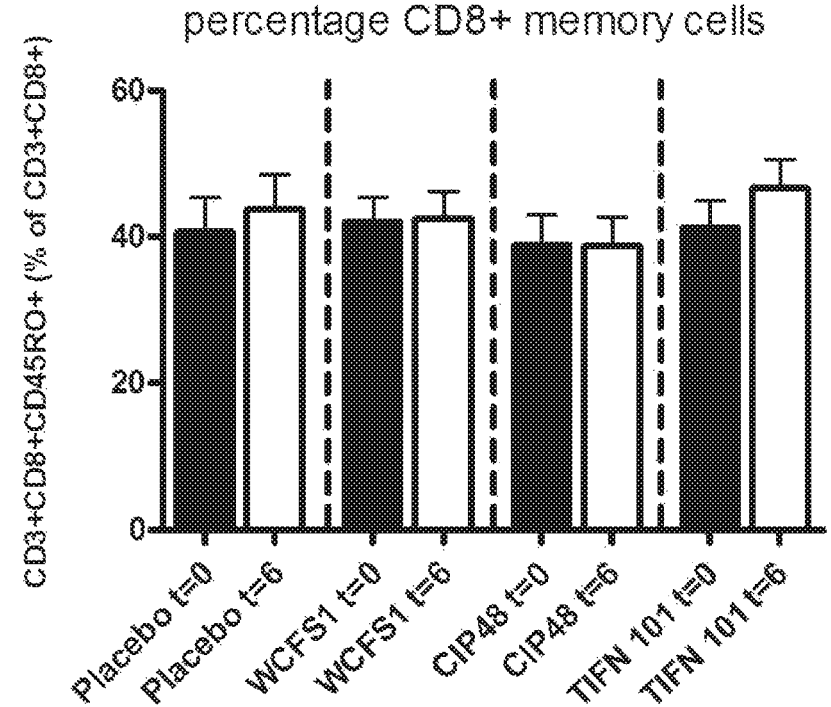
Figure 1I:
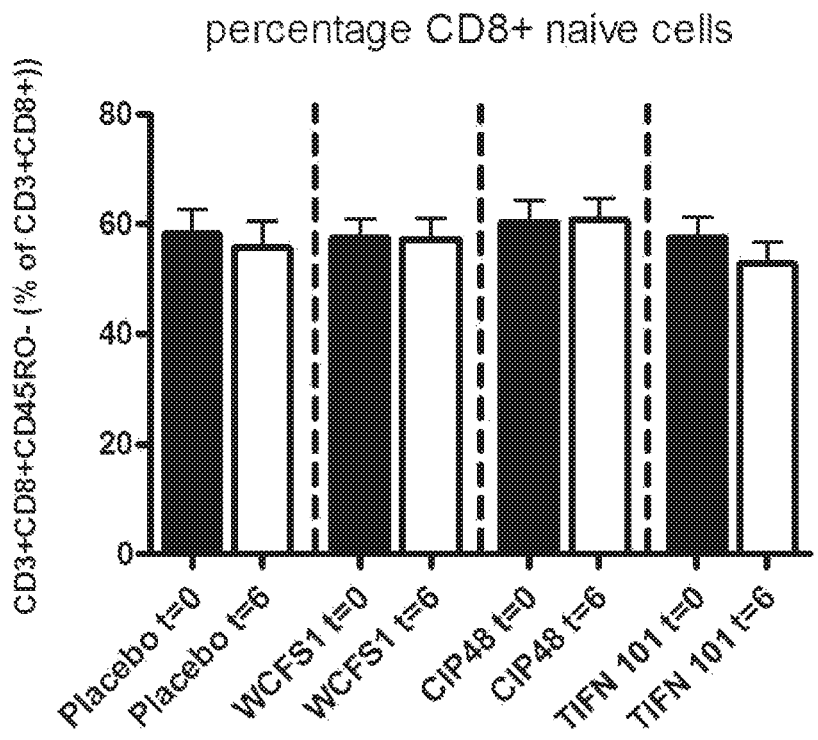
Figure 1J:
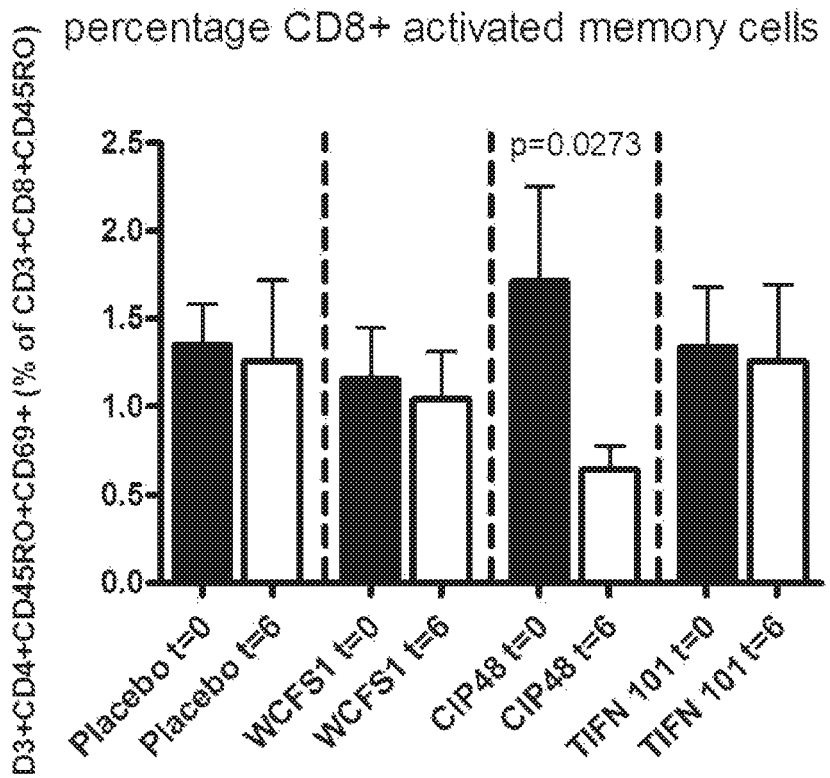

8 Claims, 12 Drawing Sheets
Specification includes a Sequence Listing.

PROBIOTIC AND NEW BIOMARKER

CROSS-REFERENCE TO RELATED APPLICATIONS

This application is a National Stage entry of International Application No. PCT/EP2015/077642, filed Nov. 25, 2015, which claims priority to European Patent Application No. 14194729.1, filed Nov. 25, 2014 and European Patent Application No. 14194725.9, filed Nov. 25, 2014.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2919208-451000_Seq-Listing-as-filed_May-23-2017.txt" created on 12 May 2017, and 8,102,576 bytes in size) is submitted concurrently with the instant application, and the entire contents of the Sequence Listing are incorporated herein by reference.

FIELD OF THE INVENTION

The present invention relates to a new probiotic with immune modulating properties and to a new biomarker.

BACKGROUND OF THE INVENTION

During recent years it has become generally accepted that adequate function of the human immune system depends on the complex interaction of the microbiota with the human mucosa (Belkaid et al., 2014; Cao et al., 2014). In normal health, nonpathogenic bacteria activate the immune system to induce tolerance to microbiota essential for energy harvesting and immune development (de Kivit et al., 2014; Geuking et al., 2014; Walker et al., 2014). However, under specific conditions immune responses may occur against microbes that contribute to the development of diseases such as IBD (Meijerink et al., 2010). Human health may benefit from more insight in how microorganisms contribute to homeostasis of immune responses and how they prevent inflammation. The hope is it will lead to design of tailored interventions.

Commensal *Lactobacilli* species may play an active role in the maintenance of homeostasis of immune responses by guiding the polarization of T-cells toward regulatory T (Treg) cells and suppression of allergy associated Th2 responses (Smelt et al., 2013). This is considered to be accomplished by the interactions of bacterial cell wall components or secreted bacterial products that interact with immune or epithelial cells in the human mucosa (Walker et al., 2014). These interactions however seem to contribute to more than just tolerance to the beneficial microbes. In many studies *Lactobacilli* have been shown to have a positive impact on immune responses as shown in several vaccination studies (Meijerink et al., 2012; Wells et al., 2011). Also, *Lactobacilli* activate more general tolerogenic cellular pathways in humans as recently shown (van Baarlen et al., 2010; van Baarlen et al., 2009).

*Lactobacilli plantarum* is a well characterized food-derived bacterium (van Baarlen et al., 2009). In previous studies it has been shown that *Lactobacilli plantarum* strains have different effects on human dendritic cells and human peripheral blood mononuclear cells (Meijerink et al., 2010; Meijerink et al., 2012; Wells et al., 2011; van Baarlen et al., 2010; van Baarlen et al., 2009; Van Hemert et al., 2010). By applying comparative genome hybridization a number of bacteriocins and cell-wall components involved in glycosylation of cell wall teichoic acids have been identified that are associated with these differential effects (Meijerink et al., 2010; Meijerink et al., 2012; Wells et al., 2011; van Baarlen et al., 2010; van Baarlen et al., 2009; Van Hemert et al., 2010; Smet et al., 2013). It is assumed that this differential expression of *Lactobacilli plantarum* genes contributes to the observed differences in activation of Toll-like receptor (TLR)2-4, CD14 antigens, and nucleotide-binding oligomerization domain-containing 2 (NOD2) (Meijerink et al., 2010). As a consequence of differences in TLR-binding, *Lactobacillus plantarum* strains induce upon incubation with monocytes or dendritic cells different quantities of the proinflammatory cytokine IL12 and the regulatory cytokine IL10 (Meijerink et al., 2010; Meijerink et al., 2012; Wells et al., 2011; van Baarlen et al., 2010; van Baarlen et al., 2009; Van Hemert et al., 2010; Smet et al., 2013; Smelt et al., 2013). The gastrointestinal barrier may be disrupted on almost a daily basis by e.g. nonsteroidal anti-inflammatory drugs (NAISDs), sports or alcohol intake and as such cause (mild) inflammation of the intestine. A mild stressor cytokine that is very common in the Western society is the consumption of an NSAID such as indomethacin. Millions are using NSAIDs for the treatment of musculoskeletal pain. A side effect of these NSAIDs is the mild inflammation of the intestine by disruption of the gastrointestinal immune barrier (Schoultz et al., 2012). As NSAIDs are used by millions worldwide there is an urgent need to treat such (mild) inflammation of the intestine.

Another issue where food derived antigens may play a role is in maintaining vaccination efficacy. It is well known that immune memory to an antigen encountered in past (some decades ago) may wane over time. When the individual encounters the antigen or pathogen associated with the antigen again, such waned immune memory may result in an insufficient response to the antigen or pathogen associated with the antigen (Deasy et al., 2013; Kerneis et al., 2014; Poorolajal et al., 2010; Schure et al., 2012).

Accordingly, there is an urgent need to preserve, maintain and/or reactivate the immune memory. This could not only revive a waned immune response, it could also render the host immune system more susceptible to vaccination protocols, which may be specifically beneficial for immune compromised individuals such as elderly. In addition, to identify and to demonstrate effects of immune modulating products, adequate biomarkers and assays are lacking. Accordingly, there is an urgent need for such biomarker and/or assay.

SUMMARY

Surprisingly, it has now been demonstrated that a specific *Lactobacillus* has immune modulating properties. Such specific *Lactobacillus* preferably also has anti-inflammatory properties.

Accordingly, in a first aspect the present invention provides a probiotic formulation comprising at least one food-grade substance and at least one probiotic bacterial strain which has at least 50% sequence identity with the genome of *Lactobacilli plantarum* TIFN 101 (deposited under number CBS 138100 at the Centraalbureau voor Schimmelcultures, Uppsalalaan 8, 3584 CT The Netherlands). Said probiotic formulation is herein referred to as a probiotic formulation according to the present invention. Said probiotic bacterial strain is herein referred to as a probiotic bacterial strain according to the present invention and has immune modulating properties and preferably also has anti-inflammatory properties.

A preferred probiotic bacterial strain according to the present invention comprises at least one polynucleotide that has at least 50% sequence identity with a polynucleotide sequence selected from the group consisting of SEQ ID NO: 1-SEQ ID NO: 174.

DETAILED DESCRIPTION OF A PREFERRED EMBODIMENT

Preferably, a probiotic bacterial strain according to the present invention comprises at least two, more preferably three, four, five, six, seven, eight, nine, ten, twenty, thirty, forty, fifty, sixty, seventy, eighty, ninety or most preferably hundred polynucleotides that each have at least 50% sequence identity with a polynucleotide sequence selected from the group consisting of SEQ ID NO: 1-SEQ ID NO: 174.

A further preferred probiotic bacterial strain according to the present invention comprises at least one polynucleotide that has at least 50% sequence identity with a polynucleotide sequence selected from the group consisting of SEQ ID NO: 176-SEQ ID NO: 256.

Preferably, a probiotic bacterial strain according to the present invention comprises at least two, more preferably three, four, five, six, seven, eight, nine, ten, twenty, thirty, forty, fifty, sixty, seventy, eighty, ninety or most preferably hundred polynucleotides that each have at least 50% sequence identity with a polynucleotide sequence selected from the group consisting of SEQ ID NO: 176-SEQ ID NO: 256.

A further preferred probiotic bacterial strain according to the present invention comprises at least one polynucleotide that has at least 50% sequence identity with a polynucleotide encoding a polypeptide with a sequence selected from the group consisting of SEQ ID NO: 260-SEQ ID NO: 340. Preferably, a probiotic bacterial strain according to the present invention comprises at least two, more preferably three, four, five, six, seven, eight, nine, ten, twenty, thirty, forty, fifty, sixty, seventy, eighty, ninety or most preferably hundred polynucleotides that each have at least 50% sequence identity with a polynucleotide encoding a polypeptide with a sequence selected from the group consisting of SEQ ID NO: 260-SEQ ID NO: 340.

The immune modulating properties can be assessed in vivo and in vitro. For a preferred assessment in vitro, Peripheral Blood Mononuclear Cells (PBMC) are isolated from blood and stimulated with an antigen and the probiotic bacterial strain or a part or an extract thereof.

An immune modulating property of a probiotic bacterial strain according to the present invention preferably is the ability to preserve, maintain and/or reactivate an immune response raised by a previous immunization and is preferably defined as the ability to maintain or increase the amount of a sub-population of PBMC within a population of PBMC. Preferably said sub-population is an antigen specific CD45RO+ population, preferably selected from CD3+/CD4+/CD45RO+ cells (memory Thelper cells), CD3+/CD4+/CD45RO+/CD69+ cells (activated memory Thelper cells), CD3+/CD8+/CD45RO+ cells (cytotoxic T cells), CD3+/CD8+/CD45RO+/CD69+ cells (activated memory T cells), CD3+/CD4+/CD45RO+/CCR7+/CD62L+ cells (central memory Thelper cells), CD3+/CD4+/CD45RO+/CCR7−/CD62L− cells (effecter memory Thelper cells). Further preferred sub-populations are CD3+/CD4+/Foxp3+ cells (Foxp3+ Thelper cells), and IFNγ and/or IL17 producing CD3+/CD4+/CD45RO+ cells (IFNγ and/or IL17 producing memory Thelper cells). Preferably, the sub-population of CD3+/CD4+/Foxp3+ cells (Foxp3+ Thelper cells) and/or CD3+/CD8+/CD45RO+/CD69+ cells (activated memory T cells) are maintained in a subject that is administered a probiotic formulation or a probiotic bacterial strain according to the present invention. Preferably, the sub-population of IFNγ and/or IL17 producing CD3+/CD4+/CD45RO+ cells (IFNγ and/or IL17 producing memory Thelper cells) is increased in a subject that is administered a probiotic formulation or a probiotic bacterial strain according to the present invention.

Preferably, the antigen is a recall antigen by purposive or non-purposive immunization, i.e. an antigen that the individual has encountered previously; more preferably, the recall antigen is selected from the group consisting of tetanus toxin, Hepatitis B antigen and Influenza. Preferably, an increase in the amount of the specific sub-population of PBMC is at least 10%, 20%, 30%, 40%, 50%, 60%, 70%, 80%, 90%, 100% (i.e. a 1-fold increase), a 2-fold increase, a 3-fold increase, a 4-fold increase, a 6-fold increase, a 10-fold increase, a 50-fold increase, a 100-fold increase, a 1000-fold increase, or at least a 10,000-fold increase. Such increase can be measured by any assay known by the person skilled in the art and is preferably measured with an assay as described herein.

A further preferred immune modulating property is enhanced cytokine production of memory Thelper cells, more preferably activated memory Thelper cells; preferably the percentage of IL-17-producing (activated) memory Th cells and/or the percentage of IFNγ-producing (activated) memory Th cells is/are increased compared to a control that has no probiotic according to the present invention administered. The increase in percentage is preferably at least 10%, 20%, 30%, 40%, 50%, 60%, 70%, 80%, 90%, 100% (i.e. a 1-fold increase), a 2-fold increase, a 3-fold increase, a 4-fold increase, a 6-fold increase, a 10-fold increase, a 50-fold increase.

A further preferred immune modulating property of a probiotic formulation or a probiotic bacterial strain according to the present invention is the induction of a change in IL10/IL12 ratio by dendritic cells when assayed according to Meijerink et al., 2010, preferably a change into a relatively high IL10/IL12 ratio. The increase in ratio is preferably at least 10%, 20%, 30%, 40%, 50%, 60%, 70%, 80%, 90%, 100% (i.e. a 1-fold increase), a 2-fold increase, a 3-fold increase, a 4-fold increase, a 6-fold increase, a 10-fold increase, a 50-fold increase.

A further preferred immune modulating property is the induction of a differential transcriptional response in duodenal mucosa. Preferably, a gene encoding a compound selected from the group consisting of immunoglobulin lambda variable 6-57, putative V-set and immunoglobulin domain-containing protein 6-like, immunoglobulin lambda variable 7-46, interferon regulatory factor 4, GDNF family, CD27, CD79a, and plasminogen activator is upregulated. The upregulation is preferably an increase of expression level of at least 10%, 20%, 30%, 40%, 50%, 60%, 70%, 80%, 90%, 100% (i.e. a 1-fold increase), a 2-fold increase, a 3-fold increase, a 4-fold increase, a 6-fold increase, a 10-fold increase, a 50-fold increase.

A further preferred immune modulating property is the upregulation of MHC-II α in the duodenal mucosa. The upregulation is preferably an increase of at least 10%, 20%, 30%, 40%, 50%, 60%, 70%, 80%, 90%, 100% (i.e. a 1-fold increase), a 2-fold increase, a 3-fold increase, a 4-fold increase, a 6-fold increase, a 10-fold increase, a 50-fold increase. The immune modulating properties according to the present invention can be combined properties of a probiotic bacterial strain according to the present invention.

A probiotic formulation according to the present invention may comprise at least one further bacterial strain, which is preferably a probiotic bacterial strain.

A probiotic formulation according to the present invention comprises at least a probiotic bacterial strain according to the present invention and at least one food-grade substance.

A food-grade substance is herein further referred to as a food-grade substance according to the present invention and is a substance suitable for consumption by a subject, preferably a human or an animal, more preferably a human. A food-grade substance may be of plant or animal origin, and may contain essential nutrients, such as carbohydrates, fats, proteins, vitamins, and/or minerals. A food-grade substance may be intended for ingestion by an organism and subsequently assimilation by the organism's cells to produce energy, maintain life, and/or stimulate growth. A food-grade substance according to the present invention includes but is not limited to a substance selected from the group consisting of a dairy-, grain-, vegetable-, fruit-, fish-, or meat-based product.

The term "based product" is herein defined that the food-grade substance is produced from a specific raw material such as dairy, grain, vegetable, fruit, fish, or meat. The food-grade substance may be based on a mixture of different raw materials e.g. a mixture of dairy and grain or a mixture of meat and fruit.

A probiotic bacterial strain may be any probiotic bacterial strain. Probiotics are live microorganisms which, when administered in adequate amounts, confer a health benefit on the host (FAO/WHO, *Evaluation of health and nutritional properties of powder milk with live lactic acid bacteria. Report of FAO/WHO expert consultation* 1-4 Oct. 2001). The most widely applied probiotics belong to the genera *Lactobacillus* and *Bifidobacterium* (Marco et al., 2006). Their beneficial effects are exerted via several mechanisms, including the modulation of the intestinal microbiota, the production of antibacterial substances, improvement of epithelial barrier function, and reduction of intestinal inflammation (Corr, et al., 2009; Saulnier et al., 2009; Saxelin et al., 2005). Probiotics are most commonly provided through ingestion of freshly fermented food products or dried bacterial preparations. The viability of probiotic strains is considered an important trait for probiotic functionality; reaching their side of action in the intestine alive is thus considered an important trait for probiotic strains (Ma et al., 2004; Gobbetti et al., 2010). The present invention provides for a probiotic bacterial strain. A preferred probiotic bacterial strain according to the present invention is a bacterial strain selected from the group consisting of the genera of *Lactobacillus, Lactococcus, Leuconostoc, Carnobacterium, Streptococcus, Bifidobacterium, Bacteroides, Eubacterium, Clostridium, Fusobacterium, Propionibacterium, Enterococcus, Staphylococcus, Peptostreptococcus,* and *Escherichia*, preferably consisting of *Lactobacillus* and *Bifidobacterium*. Preferred species of *Lactobacillus, Bifidobacterium, Streptococcus, Leuconostoc* and *Pediococcus*. are *Lactobacillus reuteri, L. fermentum, L. acidophilus, L. crispatus, L. gasseri, L. johnsonii, L. plantarum, L. paracasei, L. murinus, L. jensenii, L. salivarius, L. minutis, L. brevis, L. gallinarum, L. amylovorus, Streptococcus thermophilus, Leuconostoc mesenteroides, Pediococcus damnosus, P. acidilactici, P. parvulus, Bifidobacterium bifidum, B. longum, B. infantis, B. breve, B. adolescente, B. animalis, B. gallinarum, B. magnum,* and *B. thermophilum*. The *Lactobacillus* bacterium is preferably *Lactobacilli plantarum*, more preferably a *Lactobacilli plantarum* from the group consisting of *Lactobacilli plantarum* JDM1, ST-III, F9UP33, EITR17, D7V971 (ATCC14917) and C6VQ24, even more preferably *Lactobacilli plantarum* WCFS1 and most preferably *Lactobacilli plantarum* TIFN 101.

It is understood that replicates and/or derivatives of the deposited strains or any other strain according to the present invention are encompassed by the invention. The term "replicate" refers to the biological material that represents a substantially unmodified copy of the material, such as material produced by growth of micro-organisms, e.g. growth of bacteria in culture media. The term "derivative" refers to material created from the biological material and which is substantially modified to have new properties, for example caused by heritable changes in the genetic material. These changes can either occur spontaneously or be the result of applied chemical and/or physical agents (e.g. mutagenesis agents) and/or by recombinant DNA techniques as known in the art. When referring to a strain "derived" from another strain, it is understood that both "replicates" of that strain, as well as "derivatives" of the strain are encompassed, as long as the derived strain still retains the immunomodulating capabilities of the strain from which it was derived.

Preferably, in a probiotic formulation according to the present invention, the concentration of probiotic bacterial strains ranges from about 1 to about 99 weight percent, more preferably from about 5 to about 90 weight percent, more preferably from about 5 to about 80, more preferably from about 5 to about 70, more preferably from about 5 to about 60, more preferably from about 10, 20, 30, or 40 to about 50 weight percent with respect to the total weight of the formulation, and/or about 1 E+4, 1 E+5, or 1 E+6 to about 1 E+8, 1 E+9, 1 E+10, 1 E+11, or 1 E+12 colony forming units/ml of formulation, even more preferably about 1×10 E+6 to about 1×10 E+12 colony forming units/ml of formulation.

More preferably, in a probiotic formulation according to the present invention, the concentration of probiotic bacterial strains ranges from 1 to 99 weight percent, more preferably from 5 to 90 weight percent, more preferably from 5 to 80, more preferably from 5 to 70, more preferably from 5 to 60, more preferably from 10, 20, 30, or 40 to 50 weight percent with respect to the total weight of the formulation, and/or 1 E+4, 1 E+5, or 1 E+6 to 1 E+8, 1 E+9, 1 E+10, 1 E+11, or 1 E+12 colony forming units/ml of formulation, even more preferably 1×10 E+6 to 1×10 E+12 colony forming units/ml of formulation. A colony forming unit is a term known to the person skilled in the art and one unit typically refers to the amount of bacteria that forms one colony on a culture plate; it is a term to refer to viable bacteria.

Even more preferably, in a probiotic formulation according to the present invention, the concentration of probiotic bacterial strains ranges from about 10 to about 50 weight percent with respect to the total weight of the formulation and/or about 1 E+6 to about 1 E+12 colony forming units/ml of formulation.

The probiotic formulation or a probiotic bacterial strain according to the present invention may be in any form or state of constitution known to the person skilled in the art. The probiotic formulation or a probiotic bacterial strain according to the present invention may be part of a (compressed) tablet or pill or may be contained within another vehicle such as a container or a capsule, a gel, or a drop. A preferred vehicle is a container with a liquid volume between 0.5 and 50 ml suitable for comprising, preferably comprising a probiotic formulation or a probiotic bacterial strain according to the present invention.

The probiotic formulation or a probiotic bacterial strain according to the present invention may also conveniently be comprised in a food substance. Accordingly, in a second aspect, the present invention provides for a food product, a formulation for food enrichment, a food supplement, a nutraceutical formulation or a pharmaceutical formulation comprising a probiotic formulation or a probiotic bacterial strain according to the present invention. A food product according to the present invention is preferably a food-grade substance as described previously herein.

A food, food composition, nutraceutical formulation, formulation for food enrichment, food supplement and pharmaceutical formulation according to the present invention is herein understood to include liquids for human or animal consumption, i.e. a drink or beverage. The food, food composition, nutraceutical formulation, formulation for food enrichment, food supplement and pharmaceutical formulation may be a solid, semi-solid, semi-liquid and/or liquid food or food substance, and in particular may be a dairy product, such as a fermented dairy product, including but not limited to a yoghurt, a yoghurt-based drink, a yoghurt-like drink, a cheese or a buttermilk. Such foods may be prepared in a manner known per se, e.g. by adding a probiotic formulation or a probiotic bacterial strain according to the present invention to a suitable food or food-grade substance, in a suitable amount. In doing so, probiotic formulation or a probiotic bacterial strain according to the present invention may be used in a manner known per se for the preparation of such (fermented) food or food-grade substance, e.g. in a manner known per se for the preparation of fermented dairy products using a probiotic formulation or a probiotic bacterial strain according to the present invention. In such methods, a probiotic formulation or a probiotic bacterial strain according to the present invention may be used in addition to the micro-organism usually used, and/or may replace one or more or part of the micro-organism usually used. For example, in the preparation of fermented dairy products such as yoghurt or yoghurt-based drinks, a probiotic formulation or a probiotic bacterial strain according to the present invention may be added to or used as part of a starter culture or may be suitably added during such a fermentation.

A pharmaceutical formulation (or pharmaceutical composition) comprising a probiotic formulation or a probiotic bacterial strain according to the present invention may be for human or animal usage in human and veterinary medicine, particularly for human therapy, and comprises at least a probiotic formulation or a probiotic bacterial strain according to the present invention and a pharmaceutically accepted excipient. The pharmaceutically accepted excipient may be any such excipient known to the person skilled in the art such as a pharmaceutically or nutritionally acceptable carrier or diluent. Examples of such suitable excipient for a pharmaceutical formulation described herein may be found in the "Handbook of Pharmaceutical Excipients", 2nd Edition, (1994), Edited by A Wade and P J Weller and in "Remington's Pharmaceutical Sciences", Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include saline, glycerol, water and mixtures thereof.

A food, food composition, nutraceutical formulation, formulation for food enrichment, food supplement and pharmaceutical formulation according to the present invention is preferably present in a container with a liquid volume between 0.5 and 1000 ml. Accordingly, the present invention provides for a container with a liquid volume between 0.5 and 1000 ml comprising a food, food composition, nutraceutical formulation, formulation for food enrichment, food supplement and pharmaceutical formulation according to the present invention.

The probiotic formulation according to the present invention and/or a probiotic bacterial strain which has at least 50% sequence identity with the genome of *Lactobacillus plantarum* TIFN 101, can conveniently be used as a medicament, preferably for the treatment or prevention of intestinal inflammation.

Accordingly, in a third aspect the present invention provides for a probiotic bacterial strain according to the present invention, and/or a probiotic formulation or a pharmaceutical formulation according to the present invention, preferably as defined in the first and/or second aspect of the present invention, for use as a medicament, preferably in the treatment or prevention of intestinal inflammation.

The present invention also provides for a method of treatment of intestinal inflammation or a method of prevention of intestinal inflammation comprising administration of a probiotic bacterial strain according to the present invention, and/or a probiotic formulation or a pharmaceutical formulation according to the present invention, preferably as defined in the first and/or second aspect of the present invention.

Intestinal inflammation within the scope of the present invention may be any intestinal inflammation known to the person skilled in the art, such as but not limited to inflammation caused by nonsteroidal anti-inflammatory drugs (NAISDs), sports, alcohol intake, irritable bowel syndrome, allergy, celiac disease, inflammatory bowel disease, Crohn's disease, gastrointestinal related autoimmune diseases such as Type I diabetes.

The probiotic formulation according to the present invention and/or a probiotic bacterial strain according to the present invention, can conveniently be used for modulation of the immune system, wherein modulation of the immune system is preferably as described previously herein. Accordingly, in a fourth aspect, the present invention provides for a probiotic bacterial strain according to the present invention, and/or a probiotic formulation according to the present invention or a pharmaceutical formulation according to the present invention for use as a medicament comprising administration of an effective amount of the probiotic bacterial strain according to the present invention and/or of the probiotic formulation or a pharmaceutical formulation according to the present invention for modulating the immune system, wherein modulation of the immune system is preferably as described previously herein.

The present invention also provides for a method of modulating the immune system of a subject suffering from intestinal inflammation, comprising administration to said subject an effective amount of a probiotic bacterial strain according to the present invention and/or an effective amount a probiotic formulation according to the present invention or a pharmaceutical composition according to the present invention.

Preferably, in this aspect of the present invention, an effective amount is about 1 E+4, 1 E+5, or 1 E+6 to about 1 E+8, 1 E+9, 1 E+10, 1 E+11, or 1 E+12 colony forming units/ml of formulation, more preferably about $1 \times 10$ E+6 to about $1 \times 10$ E+12 colony forming units/ml of formulation. More preferably, an effective amount is 1 E+4, 1 E+5, or 1

E+6 to 1 E+8, 1 E+9, 1 E+10, 1 E+11, or 1 E+12 colony forming units/ml of formulation, even more preferably 1×10 E+6 to 1×10 E+12 colony forming units/ml of formulation.

Preferably, modulation of the immune system according to this aspect of the invention comprises maintenance and/or reactivation of an immune response raised by a previous immunization and/or enhancing memory T-cells generated previously by immunization, as described previously herein.

To identify and to demonstrate the effects of immune modulating products such as described in the previous aspects of the present invention, adequate biomarkers and assays are presented herein.

Provided is a method for the detection of a response to an agent comprising:
  a. stimulating PBMC from a sample of a subject with at least one antigen,
  b. identifying a sub-population of PBMC,
  c. comparing the data from (b) to data of a, preferably otherwise identically assayed, reference sample, of preferably the same subject, which reference sample has not been stimulated with the at least one antigen of (a),
wherein a difference in data identified in (c) is a measure for a response to the agent. The method is herein further referred to as an assay or a method as presented herein. An assay as presented herein preferably involves flow cytometry and preferably is a fluorescence activated cell scanning or -sorting (FACS) assay. FACS (see e.g. The Molecular Probes Handbook. A Guide to Fluorescent Probes and Labeling Technologies (I. Johnson and M. Spence (eds.) 11th Edition, Life Technologies, 2010) is a method by which the individual cells of a sample are analyzed and sorted according to their optical properties (i.e. light absorbance, light scattering, fluorescence properties, etc.) as they pass in a narrow stream in single file through a laser beam. The Fluorescence Activated Cell Sorter was invented in the late 1960s by Bonner, Sweet, Hulett, Herzenberg, and others to perform flow cytometry and cell sorting of viable cells. Becton Dickinson Immunocytometry Systems introduced the commercial machines in the early 1970s. Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. It is a useful scientific instrument, as it provides fast, objective and quantitative recording of fluorescent signals from individual cells as well as physical separation of cells of particular interest.

The cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

A wide range of fluorophores can be used as labels in flow cytometry. Fluorophores, or simply "fluors," are typically attached to an antibody that recognizes a target feature on or in the cell; they may also be attached to a chemical entity with affinity for the cell membrane or another cellular structure. Each fluorophore has a characteristic peak excitation and emission wavelength, and the emission spectra often overlap. Consequently, the combination of labels which can be used depends on the wavelength of the lamp(s) or laser(s) used to excite the fluorochromes and on the detectors available. Fluorescence-activated cell sorting provides a rapid means of isolating large numbers of fluorescently tagged cells from a heterogeneous mixture of cells.

Positive detection of a response to an agent in a flow cytometry assay as depicted here above, preferably relies on the difference, preferably quantitative difference, of a specific sub-population of PBMC between a sample stimulated with an antigen compared to a reference sample not stimulated with said antigen, as depicted here above.

A person skilled in the art is well aware of stimulation assays and using FACS as a tool for read-out. Preferably, the assays described in the examples are used in a method as presented herein.

Preferably, the difference is an increase or maintenance in the amount of the specific sub-population of PBMC. In case the sub-population does not change in a non-stimulated reference sample, the difference is preferably an increase in the amount of the specific sub-population of PBMC in the stimulated sample. In case the sub-population does not change in the non-stimulated reference sample, the difference is preferably maintenance (no change) or an increase in the amount of the specific sub-population of PBMC in the stimulated sample.

Preferably, the sub-population is a population selected from the group consisting of CD3+/CD4+ (Thelper cells), CD3+/CD4+/CD45RO− (naïve Thelper cells), CD3+/CD4+/Foxp3+ cells (Foxp3+ Thelper cells), CD3+/CD4+/CD45RO+ (memory Thelper cells), CD3+/CD4+/CD45RO+/CD69+ (activated memory Thelper cells), CD3+/CD8+/CD45RO− (naïve CD8+ cells), CD3+/CD8+/CD45RO+ (CD8+ memory T cells), CD3+/CD8+/CD45RO+/CD69+ (activated CD8+ memory T cells), CD3+/CD4+/CD45RO+/CCR7+/CD62L+ cells (central memory Thelper cells), CD3+/CD4+/CD45RO+/CCR7−/CD62L− cells (effecter memory Thelper cells).

More preferably the sub-population is an antigen specific CD45RO+ population, preferably selected from CD3+/CD4+/CD45RO+ cells (memory Thelper cells), CD3+/CD4+/CD45RO+/CD69+ cells (activated memory Thelper cells), CD3+/CD8+/CD45RO+ cells (CD8+ memory T cells), CD3+/CD8+/CD45RO+/CD69+ cells (activated memory T cells), CD3+/CD4+/CD45RO+/CCR7+/CD62L+ cells (central memory Thelper cells), CD3+/CD4+/CD45RO+/CCR7−/CD62L− cells (effecter memory Thelper cells). Further preferred sub-populations are CD3+/CD4+/Foxp3+ cells (Foxp3+ Thelper cells), and IFNγ and/or IL17 producing CD3+/CD4+/CD45RO+ cells (IFNγ and/or IL17 producing memory Thelper cells).

Preferably, in an assay as presented herein, the response is an immune response, preferably modulation of an existing immune response, more preferably an increase of an existing immune response, such existing immune response preferably being as described previously herein.

Preferably, in a method as presented herein, the agent is a food product, preferably a probiotic, more preferably the agent or part thereof comprises a membrane of a probiotic.

Preferably, in a method as presented herein, the sample comprises a bodily fluid; preferably the sample is a blood sample.

A blood sample in the context of the present invention preferably is a sample of whole blood or of a sub-population of cells of whole blood. Sub-populations of cells of whole blood include but are not limited to PBMC or a sub-population thereof such as lymphocytes, monocytes, and macrophages. PBMC are a critical component of the immune system to fight infection and adapt to intruders.

Preferably, in a method as presented herein, the at least one antigen in (a) is selected from the group consisting of a general T cell stimulator such as a superantigen, a Protein Kinase A (PKA) stimulator such as a lectin, a recall antigen, i.e. an antigen that the individual has encountered previously, preferably selected from the group consisting of tetanus toxin, Hepatitis B antigen and Influenza, or the agent or a part thereof.

Preferably, in a method as presented herein, the at least one antigen of (a) comprises at least:
  a. a recall antigen such as tetanus toxin, a Hepatitis B antigen or an Influenza antigen, and
  b. the agent or a part thereof.

Preferably, in a method presented herein, the sub-population is a population selected from the group consisting of CD3+/CD4+ (Thelper cells), CD3+/CD4+/CD45RO− (naïve Thelper cells), CD3+/CD4+/Foxp3+ cells (Foxp3+ Thelper cells), CD3+/CD4+/CD45RO+ (memory Thelper cells), CD3+/CD4+/CD45RO+/CD69+ (activated memory Thelper cells), CD3+/CD8+/CD45RO− (naïve CD8+ cells), CD3+/CD8+/CD45RO+ (CD8+ memory T cells), CD3+/CD8+/CD45RO+/CD69+ (activated CD8+ memory T cells), CD3+/CD4+/CD45RO+/CCR7+/CD62L+ cells (central memory Thelper cells), CD3+/CD4+/CD45RO+/CCR7−/CD62L− cells (effecter memory Thelper cells).

More preferably the sub-population is an antigen specific CD45RO+ population, preferably selected from CD3+/CD4+/CD45RO+ cells (memory Thelper cells), CD3+/CD4+/CD45RO+/CD69+ cells (activated memory Thelper cells), CD3+/CD8+/CD45RO+ cells (CD8+ memory T cells), CD3+/CD8+/CD45RO+/CD69+ cells (activated memory T cells), CD3+/CD4+/CD45RO+/CCR7+/CD62L+ cells (central memory Thelper cells), CD3+/CD4+/CD45RO+/CCR7−/CD62L− cells (effecter memory Thelper cells). Further preferred sub-populations are CD3+/CD4+/Foxp3+ cells (Foxp3+ Thelper cells), and IFNγ and/or IL17 producing CD3+/CD4+/CD45RO+ cells (IFNγ and/or IL17 producing memory Thelper cells).

Preferably, in a method as presented herein, the identification of the sub-population of PBMC comprises flow cytometry analysis as depicted here above; preferably the identification of the sub-population of PBMC comprises quantification. Quantification in an assay as presented herein, preferably relates to determining the percentage of one or more sub-populations of PBMC, preferably of at least one sub-population selected form the group consisting of CD3+/CD4+ (Thelper cells), CD3+/CD4+/CD45RO− (naïve Thelper cells), CD3+/CD4+/Foxp3+ cells (Foxp3+ Thelper cells), CD3+/CD4+/CD45RO+ (memory Thelper cells), CD3+/CD4+/CD45RO+/CD69+ (activated memory Thelper cells), CD3+/CD8+/CD45RO− (naïve CD8+ cells), CD3+/CD8+/CD45RO+ (CD8+ memory T cells), CD3+/CD8+/CD45RO+/CD69+ (activated CD8+ memory T cells), CD3+/CD4+/CD45RO+/CCR7+/CD62L+ cells (central memory Thelper cells), CD3+/CD4+/CD45RO+/CCR7−/CD62L− cells (effecter memory Thelper cells).

More preferably the sub-population is an antigen specific CD45RO+ population, preferably selected from CD3+/CD4+/CD45RO+ cells (memory Thelper cells), CD3+/CD4+/CD45RO+/CD69+ cells (activated memory Thelper cells), CD3+/CD8+/CD45RO+ cells (CD8+ memory T cells), CD3+/CD8+/CD45RO+/CD69+ cells (activated memory T cells), CD3+/CD4+/CD45RO+/CCR7+/CD62L+ cells (central memory Thelper cells), CD3+/CD4+/CD45RO+/CCR7−/CD62L− cells (effecter memory Thelper cells). Further preferred sub-populations are CD3+/CD4+/Foxp3+ cells (Foxp3+ Thelper cells), and IFNγ and/or IL17 producing CD3+/CD4+/CD45RO+ cells (IFNγ and/or IL17 producing memory Thelper cells).

Further provided is the use of a sub-population of PBMC as a biomarker for efficacy testing of immune modulating agents. The term biomarker (or biological marker) refers to a distinct biochemical, genetic, or molecular characteristic or substance that is an indicator of a particular biological condition or process. Within the context of the present invention, a sub-population of PBMC as defined herein is used as biomarker.

Preferably, the immune modulating agent is a food product, preferably a probiotic such as described previously herein. Preferably, the sub-population of PBMC one such as previously described herein; preferably, the sub-population is a population selected from the group consisting of CD3+/CD4+ (Thelper cells), CD3+/CD4+/CD45RO− (naïve Thelper cells), CD3+/CD4+/Foxp3+ cells (Foxp3+ Thelper cells), CD3+/CD4+/CD45RO+ (memory Thelper cells), CD3+/CD4+/CD45RO+/CD69+ (activated memory Thelper cells), CD3+/CD8+/CD45RO− (naïve CD8+ cells), CD3+/CD8+/CD45RO+ (CD8+ memory T cells), CD3+/CD8+/CD45RO+/CD69+ (activated CD8+ memory T cells), CD3+/CD4+/CD45RO+/CCR7+/CD62L+ cells (central memory Thelper cells), CD3+/CD4+/CD45RO+/CCR7−/CD62L− cells (effecter memory Thelper cells).

More preferably the sub-population is an antigen specific CD45RO+ population, preferably selected from CD3+/CD4+/CD45RO+ cells (memory Thelper cells), CD3+/CD4+/CD45RO+/CD69+ cells (activated memory Thelper cells), CD3+/CD8+/CD45RO+ cells (CD8+ memory T cells), CD3+/CD8+/CD45RO+/CD69+ cells (activated memory T cells), CD3+/CD4+/CD45RO+/CCR7+/CD62L+ cells (central memory Thelper cells), CD3+/CD4+/CD45RO+/CCR7−/CD62L− cells (effecter memory Thelper cells). Further preferred sub-populations are CD3+/CD4+/Foxp3+ cells (Foxp3+ Thelper cells), and IFNγ and/or IL17 producing CD3+/CD4+/CD45RO+ cells (IFNγ and/or IL17 producing memory Thelper cells).

Definitions

The genome of *Lactobacilli plantarum* TIFN 101 is the genome of the strain deposited under number CBS 138100 at the Centraalbureau voor Schimmelcultures, Uppsalalaan 8, 3584 CT The Netherlands. SEQ ID NO: 175 represents a scaffold of 174 contigs of TIFN 101 and is for the context of the present invention construed as the preferred genome sequence of TIFN 101.

"Sequence identity" or "identity" in the context of amino acid- or nucleic acid-sequence is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. In all embodiments of the present invention, at least 50% sequence identity is to be construed as preferably at least 50%, more preferably 55%, 60%, 65%, 70%, 75%, 80%, 81%, 82%, 83%, 84%, 85%, 86%, 87%, 88%, 89%, 90%, 91%, 92%, 93%, 94% 95%, 96%, 97%, 98%, 99% and most preferably at least 100% sequence identity with the genome of *Lactobacilli plantarum* TIFN 101, or with a polynucleotide sequence selected from the group consisting of SEQ ID NO: 1-SEQ ID NO: 174 or with a polynucleotide encoding a polypeptide with a sequence selected from the group consisting of SEQ ID NO: 245-SEQ ID NO: 327. Within the present invention, sequence identity with a particular sequence preferably means sequence identity over the entire length of said particular polypeptide or polynucleotide sequence. The sequence information as provided herein should not be so narrowly construed as to require inclusion of erroneously identified bases. The skilled person is capable of identifying such erroneously identified bases and knows how to correct for such errors.

"Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide is represented by a nucleotide sequence. A polypeptide is represented by an amino acid sequence.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

All patent and literature references cited in the present specification are hereby incorporated by reference in their entirety.

FIGURE LEGENDS

FIG. 1. Effects of three *L. plantarum* strains on frequency of different CD4+ (a-f) and CD8+ (g-j) T-cell population in the systemic circulation (n=9). Statistical significance was calculated using the Students t-test.

FIG. 2. Effects of three *L. plantarum* strains on frequency of IL21 (a), IL17 (b), IL4 (c), and IFNγ-producing (d) superantigen (SEB) stimulated memory-Th cells (n=9). Statistical significance was calculated using the Students t-test.

FIG. 3. Effects of three *L. plantarum* strains on frequency of IL21 (a), IL17 (b), IL4 (c), and IFNγ-producing (d) *Staphylococcus aureus* enterotoxin B superantigen (SEB) stimulated memory-CD45RO+ Th cells (n=9). Statistical significance was calculated using the Students t-test.

FIG. 4. Effects of three *L. plantarum* strains on frequency of IL21 (a), IL17 (b), IL4 (c), and IFNγ-producing (d) tetanus toxoid (TT) stimulated memory-CD45RO+ Th cells (n=9). Statistical significance was calculated using the Students t-test.

FIG. 5. The Flowchart of microarray analysis (a) and the number of unique genes that are regulated in the intestinal biopsis of the human consumers of three different *L. plantarum* strains (*L. plantarum* WCFS1 (WCFS1), *L. plantarum* CIP104448 (CIP48), *L. plantarum* TIFN 101. Intensity >20 on at least 5 arrays, interquartile range >0.2, at least 7 probes per gene. (b) Venn diagram chart of the number of upregulated and (c) downregulated genes in the intestinal biopsies after consumption of *l. plantarum* and indomethacin.

EXAMPLES

The present invention is further described by the following examples which should not be construed as limiting the scope of the invention.

Unless stated otherwise, the practice of the invention will employ standard conventional methods of molecular biology, virology, microbiology or biochemistry.

Such techniques are described in Sambrook et al. (1989) *Molecular Cloning, A Laboratory Manual* ($2^{nd}$ edition), Cold Spring Harbor Laboratory, Cold Spring Harbor Laboratory Press; in Sambrook and Russell (2001) *Molecular Cloning: A Laboratory Manual*, Third Edition, Cold Spring Harbor Laboratory Press, NY; in Volumes 1 and 2 of Ausubel et al. (1994) *Current Protocols in Molecular Biology, Current Protocols*, USA; and in Volumes I and II of Brown (1998) *Molecular Biology LabFax*, Second Edition, Academic Press (UK); *Oligonucleotide Synthesis* (N. Gait editor); *Nucleic Acid Hybridization* (Hames and Higgins, eds.).

Example 1

Differential Human Mucosal Transcriptomic and Immune Responses to Three Probiotic Strains; Insight in How Probiotics Contribute to Immunity in Healthy Individuals Materials and Methods
Bacterial Strains and Growth Conditions

*Lactobacilli plantarum* WCFS1 (Kleerebezem et al., 2003), *Lactobacilli plantarum* CIP104448 (CIP48), and *Lactobacilli plantarum* TIFN 101 were cultured at 37° C. in Man, Rogosa and Sharpe (MRS) medium (Merck). To obtain stationary-phase cultures, bacteria were cultured overnight. Maltodextrin and glucose were added to a final concentration of 20% and 2% (wt/vol), respectively, to obtain bacterial preparations (WCFS1, $2.6 \times 10^9$ CFU; CIP48, $2.4 \times 10^9$ CFU; TIFN 101, $5.6 \times 10^9$ CFU); placebo controls only contained the two sugars. Bacteria and placebo materials were prepared such that they contained similar final sugar concentrations. Detailed protocols for culturing, harvesting, freeze-drying, storing, and viable count determining of *Lactobacillus* species can be found in Smelt et al. 2012.

Volunteers and Interventions

This study was approved by the University Hospital Maastricht Ethical Committee and was conducted in accordance with the principles of the Declaration of Helsinki. All subjects gave their written informed consent before their inclusion in the study. Ten healthy volunteers, 7 female and 3 male (26.3±10.1 years, BMI of 21.8±2.40 kg/m$^2$), without a history of gastrointestinal symptoms and free of any form of medication, were tested on four separate occasions (three bacterial interventions and one placebo control, randomly chosen) in a randomized placebo-controlled cross-over study. The volunteers consumed habitual diet during the study period and were asked to fill in a gastrointestinal symptoms diary. Three days before the intervention a blood sample was taken to obtain baseline values. The night before the start of the supplements intake period the volunteers ingested 75 mg of indomethacin. At the starting day the volunteers ingested another dosage of 50 mg indomethacin conform previously established protocol to establish mild gastrointestinal stress (Troost et al., 2003). Subsequently, the volunteers consumed the probiotic or placebo supplements for a period of 7 days during lunch and during dinner; *L. plantarum* WCFS1 ($2.6^{10}$ colony forming units (cfu) per shot), *L. plantarum* CIP104448 ($2.4^{10}$ cfu/shot), *L. plantarum* TIFN 101 ($5.9^{10}$ cfu/shot) or placebo. Neither the volunteers nor the researchers knew which subject received the *L. plantarum* strains or the placebo (double-blinded study); the vials containing bacteria or placebo control were non-transparent. On the $7^{th}$ day, tissue samples were obtained from the horizontal part of the duodenum by standard flexible gastroduodenoscopy at approximately 15 cm distal to the pylorus. The duodenal mucosa was chosen as this is the first intestinal segment coming in contact with the bacteria, minimizing the adaptive changes microbes might go through during passage of the intestinal tract. Also, the duodenum is readily accessible for mucosal tissue sampling. Finally, the duodenum contains the lowest endogenous microbiota colonization level, ensuring that the measured responses are as specific as can be achieved. The interventions were performed with an interval of 4 weeks to allow a wash-out period and to allow healing of the biopsy-sampling region.

Cell Staining

The various dilutions of the antibodies and other reagents used for cell staining are listed in Table 1.

Blood was collected in EDTA containing tubes and processed for FACS analysis. The following antibodies were used for staining of the T cell sub-populations: Pacific Blue-conjugated anti-CD3 (clone UCHT1; BD Pharmingen), PerCP conjugated anti-CD8 (clone SK1, Biolegend), APC-Cy7-conjugated anti-CD69 (clone FN50, BD Pharmingen), APC-conjugated anti-FoxP3 (clone 206D, eBioscience), biotin-conjugated anti-CD45RO (UCHL1, Biolegend) with Pacific orange conjugated streptavidin (Invitrogen). Isotype controls were purchased from the same company as the antibodies and used in the same dilution as the antibody.

For intracellular cytokine staining of T cells we used: PE-Cy7 conjugated anti-IL4 (MP4-25D2, Biolegend), Alexa488-conjugated anti-IL-17A (clone eBio64DEC17; eBioscience), PE-conjugated anti-IL-21 (clone eBio3A3-N2; eBioscience), Alexa700-conjugated anti-IFNγ (clone B27; BD Pharmingen), For staining of the NK cell populations we used: APC-conjugated anti-CD56 (clone MEM-188, Ebioscience), EFluor450-conjugated anti-CD16 (clone CB16, eBioscience), PE-conjugated anti-CD335 (clone 9E2, Biolegend), PE-Cy7-conjugated anti-CD161 (clone HP-3G10, eBioscience) T-cell polarization was studied after three types of stimulations of the T-cells. It was done by (i) aspecific stimulation with PMA/Ca$^{2+}$ or superantigen (SEB) to study whether the total responsiveness was influenced by probiotic treatment, by (ii) stimulation with cell extracts of the specific *L. plantarum* strains in order to investigate whether specific immune responses against the probiotic was stimulated, and (iii) by stimulating with an antigen to which all volunteers were vaccinated, tetanus toxoid (TT), to study possible stimulation of specific memory responses.

After blood sampling, 200 µl of blood was diluted with 200 µl of RPMI1640 supplemented with 10% fetal calf serum (FCS) and incubated with either PMA (Phorbol myristate acetage; 80 nM Sigma-Aldrich, Steinheim, Germany) and Ca2+ (4 µM) (4 hr), *Staphylococcus aureus* enterotoxin B SEB (5 µg/mL Sigma, Deisenhofen, Germany) (24 hr), TT (tetanus toxoid; 1.5 Lf/mL) (24 hr) or bacterial lysates (30 µg/mL) (24 hr). Stimulation with bacterial lysates was according to the administered strain and performed one week after treatment. After the treatment week with *L. plantarum* WCFS1, samples were stimulated with cell extracts of *L. plantarum* WCFS1; after the treatment week with *L. plantarum* CIP104448, samples were stimulated with cell extracts of *L. plantarum* CIP104448; after the treatment week with *L. plantarum* TIFN 101, samples were stimulated with cell extracts of *L. plantarum* TIFN 101. These cell extracts were made by repeated freeze-thawing of the probiotics.

After stimulation, red blood cells were lysed with ammonium chloride. After washing (PBS with 2% FCS), cells were incubated with different antibody cocktails.

Staining for T cells and T cell subsets: Cells were incubated with an antibody cocktail consisting of anti-CD3, anti-CD8 and anti-CD45RO for 30 minutes in the dark on ice.

After washing with washing buffer, cells were incubated with streptavidine Pacific Orange (1:100 Invitrogen) for 15 minutes on ice. After washing and spinning down, pelleted cells were resuspended in Fixation/Permeabilization solution (eBioscience, 0.1% saponin and 0.009% sodium azide) for 45 minutes on ice. After washing in Perm solution (eBioscience), cells were incubated in mouse serum for 15 minutes to prevent non-specific binding, followed by incubation with the cytokine antibody mix (anti-IL-4, anti-IFNγ, anti-IL-17 and anti-IL21) or an isotype cytokine mix for 30 minutes on ice. After washing with Permeabilization solution (3 times) cells were resuspended in wash-buffer and measured by flow cytometry within 24 hrs.

Staining for NK cells: Cells were incubated with an antibody cocktail consisting of anti-CD3, anti-CD16, anti-CD56, anti-CD335 and anti-CD161 (NK cell staining), or with isotype control cocktail for NK cells consisting of anti-CD3, anti-CD16, anti-CD56 and isotype controls for anti-CD335 and CD161 for 30 minutes in the dark on ice. After washing with washing buffer, cells were fixed in FACS lysing solution (BD Biosciences, phosphate buffered saline (PBS) containing 2% heat-inactivated fetal calf serum (FCS)) for 30 minutes on ice. After washing, cells were suspended in washing buffer and measured by flow cytometry on a Becton and Dickinson LSRII within 24 hrs; at least 500,000 events were recorded per sample.

TABLE 1

| # | Reactivity | Isotype | Label | Dilution | Company |
|---|---|---|---|---|---|
| 1A | CD3 | mIgG1 (UCTH1) | Pac Blue | 1:25 | BD 558117 |
| 2 | CD8 | mIgG1 (SK1) | PerCP | 1:25 | BD 345774 |
| 4 | IL17A | mIgG1 (eBio64DEC17) | Alexa488 | 1:25 | eBio 53-7179 |
| 5 | IL21 | mIgG1 (eBio3A3-N2) | PE | 1:25 | eBio 12-7219 |
| 6 | IFNg | mIgG1 (B27) | Alexa700 | 1:100 | BD 557995 |
| 7 | CD69 | mIgG1 (FN50) | APC-Cy7 | 1:25 | BD 557756 |
| 8 | FoxP3 | mIgG1 (206D) | APC | 1:25 | eBio 9017-4776-220 |
| 9 | CD45R0 | mIgG2a (UCHL1) | Biotin | 1:25 | BioLegend 304220 |
| 10 | Streptavidin | | Pac Orange | 1:100 | Invitrogen |
| 11 | CD3 | mIgG1 (UCHT1) | PerCP | 1:30 | BioLegend 300428 |
| 12 | CD16 | mIgG1 (CB16) | eFluor450 | 1:10 | eBio 48-0168-42 |
| 13 | CD56 | mIgG2a (MEM-188) | APC | 1:25 | eBio 17-0569-42 |
| 14 | CD335 | mIgG1 (9E2) | PE | 1:7.5 | BioLegend 331908 |
| 15 | CD161 | mIgG1 (HP-3G10) | PE-Cy7 | 1:20 | eBio 25-1619-42 |
| 17 | — | Mouse IgG1 | PE | 1:62.5 | BioLegend 400112 |
| 18 | — | Mouse IgG1 | PE-Cy7 | 1:20 | eBio 25-4714 |
| 20 | IL4 | rIgG1 (MP4-25D2) | PE-Cy7 | 1:25 | BioLegend 500824 |

RNA Isolation and Microarray

Total RNA was isolated from the duodenal biopsies by using Trizol reagent (1 ml) (Invitrogen, Breda, NL). Thereafter RNA was purified using the Qiagen RNeasy Micro kit (Qiagen, Venlo, NL). RNA was quantified on a NanoDrop ND-1000 spectrophotometer (Isogen Life Science, De Meer, The Netherlands) RNA quality was checked using an Agilent 2100 bioanalyzer (Agilent Technologies, Amsterdam, NL). RNA was judged suitable for array hybridization only if samples exhibited intact bands corresponding to 18S and 28S ribosomal subunits and displayed no chromosomal peaks or RNA degradation products.

Total RNA (100 ng) was used for whole transcript cDNA synthesis by using the Ambion WT expression kit (Life Technologies, Bleiswijk, The Netherlands) and subsequently labelled by using the Affymetrix GeneChip WT Terminal Labelling Kit (Affymetrix, Santa Clara Calif.). Samples were hybridized to human whole genome Affymetrix GeneChip Human Gene 1.1 ST arrays, washed, stained, and scanned on an Affymetrix GeneTitan instrument. Details on array handling can be found in the Affymetrix GeneTitan Instrument User Guide for Expression Array Plates (P/N 702933 Rev.2).

Microarray Data Analysis

Microarray analysis was performed by applying MAD-MAX for statistical analysis (Lin et al 2011, J Integr Bioinform, PMID 21778530). Quality control was performed. All arrays met the criteria. The probes on the Human Gene 1.1 ST arrays were redefined according to Dai et al (2005, Nucleic Acids Res PMID 16284200) based on the NCBI Entrez database (CDF version 15.1). In this way the Human Gene 1.1 ST array targets 19,682 unique genes. Normalized expression values were obtained from the raw intensity values by using the robust multiarray analysis preprocessing algorithm available in the library AffyPLM using default setting (Irizarry et al, Biostatistics, 2003, PMID 12925520). Microarray data were filtered, and probe sets with at least 5 probes and expression values higher than 20 on at least 5 arrays, and a interquartile range >0.2 (log 2 scale) across all samples were and selected for further statistical analysis. In addition, an Inter Quartile Range (IQR) cut-off of 0.2 was used to filter out genes that showed no variation between the conditions. Differentially expressed genes were identified by using linear models, applying moderated t-statistics that implemented empirical Bayes regularization of standard errors in the library limma (Smyth et al., 2004). To adjust for both the degree of independence of variances relative to the degree of identity and relation between variance and signal intensity, the moderated t-statistic was extended by a Bayesian hierarchical model to define an intensity-based moderated t-statistic (Sartor et al, 2006, BMC Bioinformatics PMID 17177995). Genes were defined as significantly changed when the P value was <0.05 for pairwise comparisons.

Pathway Analysis

Geneset enrichment analysis (GSEA; at world wide web: broad.mit.edu/gsea/) was performed using MADMAX and genesets with a false discovery rate (FDR) <0.2 were considered significantly enriched. GSEA takes into account the broader context in which gene products function, namely in physically interacting networks such as biochemical, metabolic, or signal transduction routes, and has the advantage that it is unbiased, because no gene selection step is used (Subramanian et al., 2005. Possible transcription factors playing a role in the activation and inhibition of genes were identified using Upstream Regulator Analysis in Ingenuity Pathway Analysis (IPA; Ingenuity Systems, Redwood City, Calif.).

Genome Sequencing and Annotation

The L. plantarum strain CIP104448 was obtained from the NIZO culture collection (Meijerink et al., 2010). For DNA preparation, 2 ml of overnight culture was pelleted, washed and resuspended in TES buffer (N-[tris(hydroxymethyl)methyl]-2-aminoethanesulfonicacid). Cells were lysed with lysozyme (360 mg/ml) and mutanolysin (140 U/ml) by incubation for 2 h at 37° C. Subsequently 300 µl water was added and 80 µl of 20% SDS solution. The DNA extraction was done using phenol/chloroform (3×). The DNA was precipitated with isopropanol and washed with 70% ethanol. Samples were treated with 100 µg/ml RNAse (Sigma) during 1 hour at 37° C. DNA paired-end libraries with barcoding were made and sequenced using Illumina technology (Baseclear Leiden, NL). The contig sequences were submitted to the RAST automatic annotation server, which provided ORF calling and automatic annotation. The annotated contigs of CIP48 and TIFN 101 were ordered by comparing them to the circular template genome of L. plantarum WCFS1, and comparing them to each other. Contigs/genes which did not match to the WCFS1 genome were annotated in more detail using BLASTP (http://blast.ncbi.nlm.nih.gov/) and InterProscan (http://www.ebi.ac.uk/interpro/). Ortholog groups (OGs) in the 3 genomes were determined using OrthoMCL (www.orthomcl.org/).

Statistics

Flow cytometry data results are expressed as the mean±standard error of the mean (SEM). Normal distribution of the data sets was confirmed by the Kolmogorov-Smirnov test. The two-sided Students t-test was used to determine changes in immune cell populations after probiotic treatment. Gene expression data are depicted as the medium (range). The two-sided Mann Whitney U-test was used to determine changes in expression profiles after probiotic treatment in vivo. P-values<0.05 (*) were considered statistically significant.

Results

Human Trial

None of the volunteers experienced any discomfort during or after the 7 days consumption period. Before the start of the trial (day 0), and at day 7 blood samples were taken to study the effect of probiotic consumption on T-cell polarization. Also at day 7 biopsies were taken by standard flexible gastroduodenoscopy, and total RNA was isolated and hybridized to whole-genome expression microarrays. Quality control of the hybridizations and primary data analysis were performed according to strict criteria to ensure that the array data were of the highest possible quality.

Differential Peripheral Responses Induced by L. plantarum

L. plantarum WCFS1, L. plantarum CIP104448, and L. plantarum TIFN 101 were selected from a series of 42 individual L. plantarum strains which were assayed for the levels of IL-10 and IL12 they induced from dendritic cells (Meijerink et al., 2010). L. plantarum WCFS1 is characterized by a relative low IL10/IL12 ratio and classified as proinflammatory, L. plantarum CIP104448, does not change the IL10/IL12 ratio when compared to medium control and is therefore classified as neutral and L. plantarum TIFN 101 induces a relative high IL10/IL12 ratio and is therefore classified as anti-inflammatory (Meijerink et al., 2010).

Cell Frequencies After 6 Days of Treatment with L. plantarum

We did not observe differences in the frequencies of the total percentage of CD3+ cells, the CD3+/CD4+ cells (naïve or memory), or the activated memory CD3−/CD4+ cells after treatment with either L. plantarum strain. However, the percentage of CD4+/Foxp3 positive cells was significantly decreased following placebo and CIP 48 treatment, but not after WCFS1 and TIFN 101 treatment (FIG. 1a-f). Moreover, although we did not find an effect of treatment on CD3+/CD8+ naïve and memory cells, activated memory cells were statistically significantly decreased by CIP48 treatment only (P<0.01) (FIG. 1g-j).

Treatment did not affect total NK cell numbers or NKT numbers. There was also no change in the percentages of the NK cell subtypes (i.e. CD56hi and CD56dim), while the expression of CD161 (KLRB1), mediating cytotoxicity (Jacobs et al., 2001; Tarazona et al., 2002), was also not affected by the L. plantarum treatments.

T-cell polarization was studied after three types of stimulations of the T-cells. It was done by (i) non-specific stimulation with PMA/$Ca^{2+}$ or superantigen (SEB) to study whether the total responsiveness was influenced by L. plantarum treatment, by (ii) stimulation with cell extracts of the specific L. plantarum strains in order to investigate whether specific immune responses against the L. plantarum was stimulated, and (iii) by stimulation with a previously administered vaccine antigen (TT) to study possible stimulation of specific memory responses.

After non-specific stimulation with PMA/Ca-ionophore or SEB, we studied the percentage of IFNγ, IL-4, Il-17 or IL-21 positive Th cells and memory Th cells. Treatment with placebo or the administered L. plantarum strains did not influence cytokine production of the total population of Th cells or of the Th memory cells after non-specific stimulation with PMA/Ca-ionophore (results not shown). Although after SEB stimulation no differences were found in cytokine production of the total Th cell population after the three L. plantarum treatments (results not shown), we did observe differences in cytokine production of the Th memory cells after L. plantarum treatment. After stimulation with SEB (FIG. 2a-d), we observed a decreased percentage of IL-17 producing activated memory Th cells following treatment with CIP48 and an increased percentage of IL-17 producing activated memory Th cells after treatment with TIFN 101

Figure 2A:
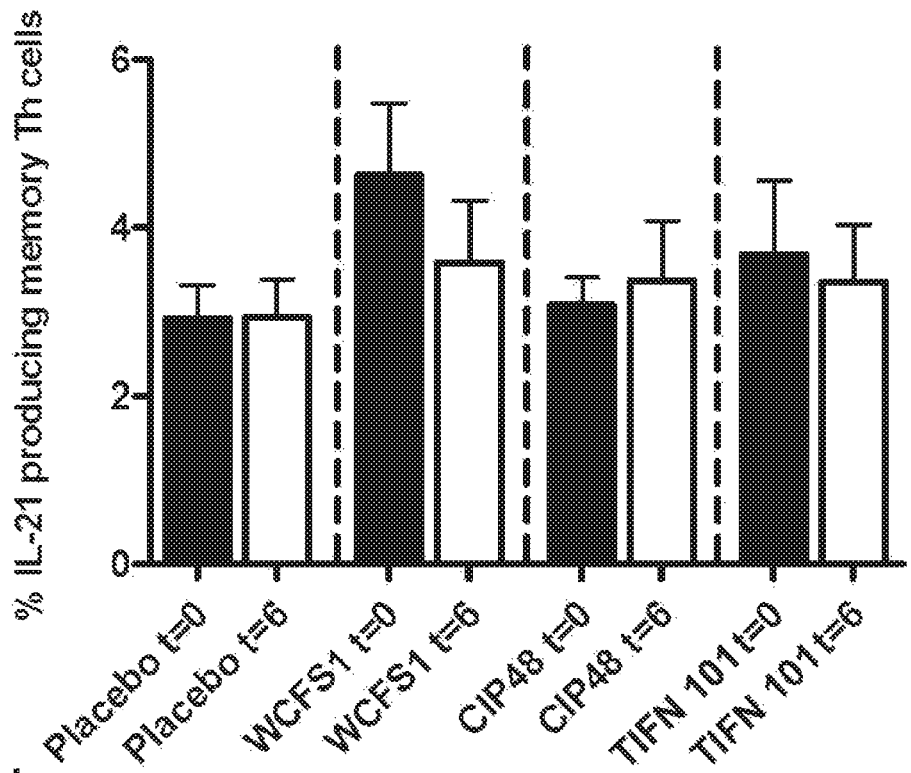
Figure 2B:
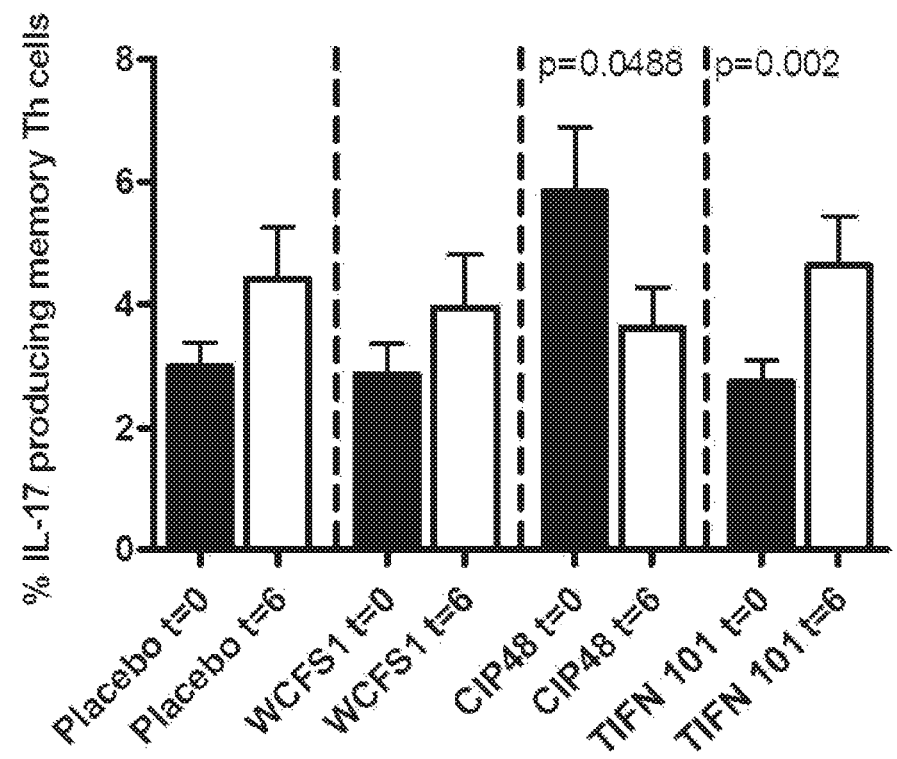
Figure 2C:
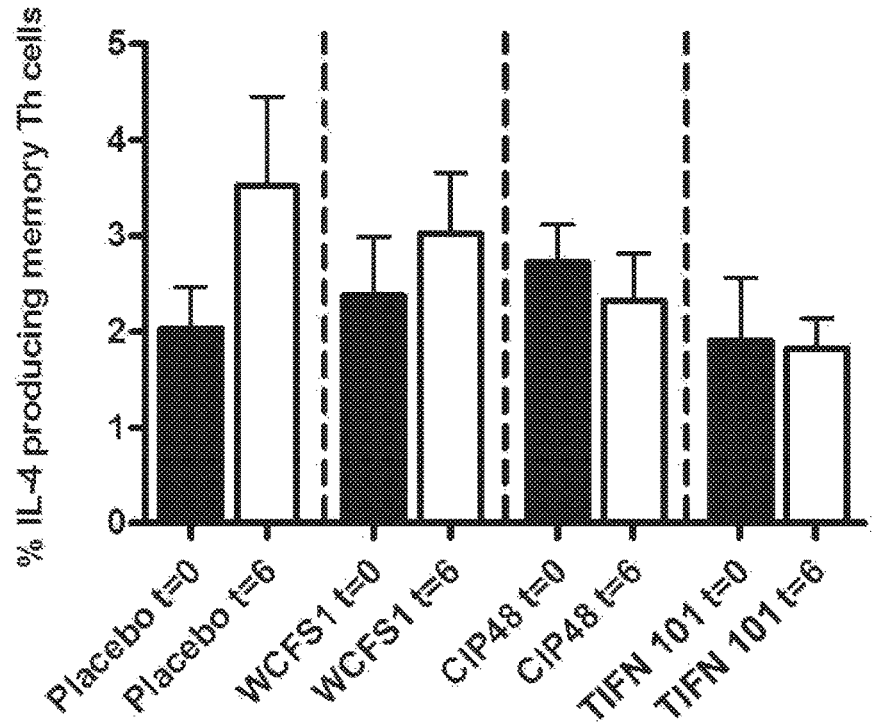
Figure 2D:
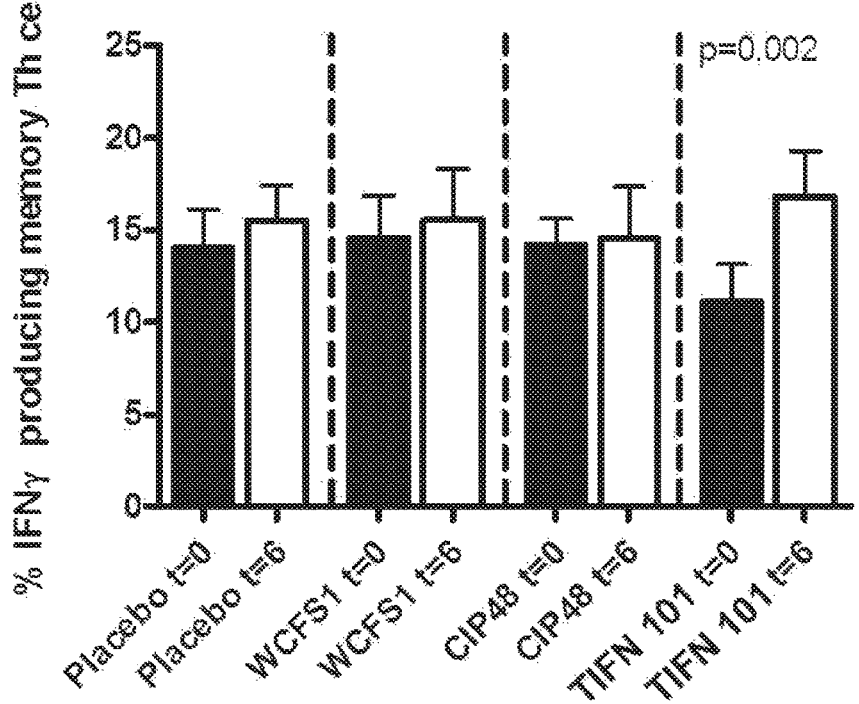
Figure 3A:
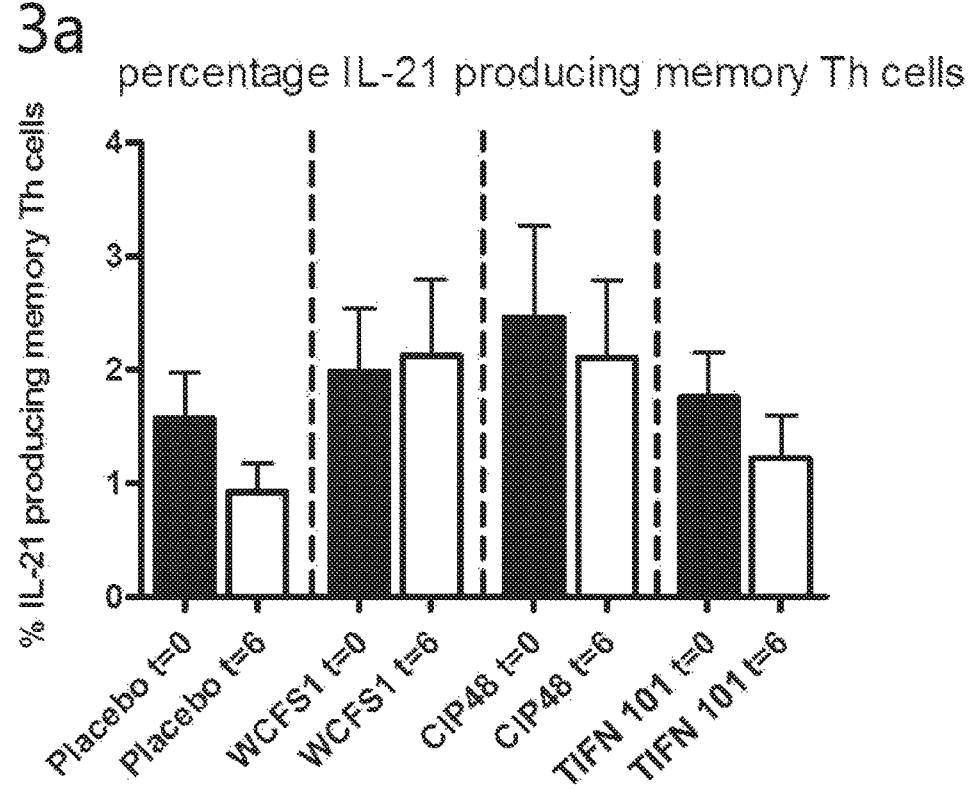
Figure 3B:
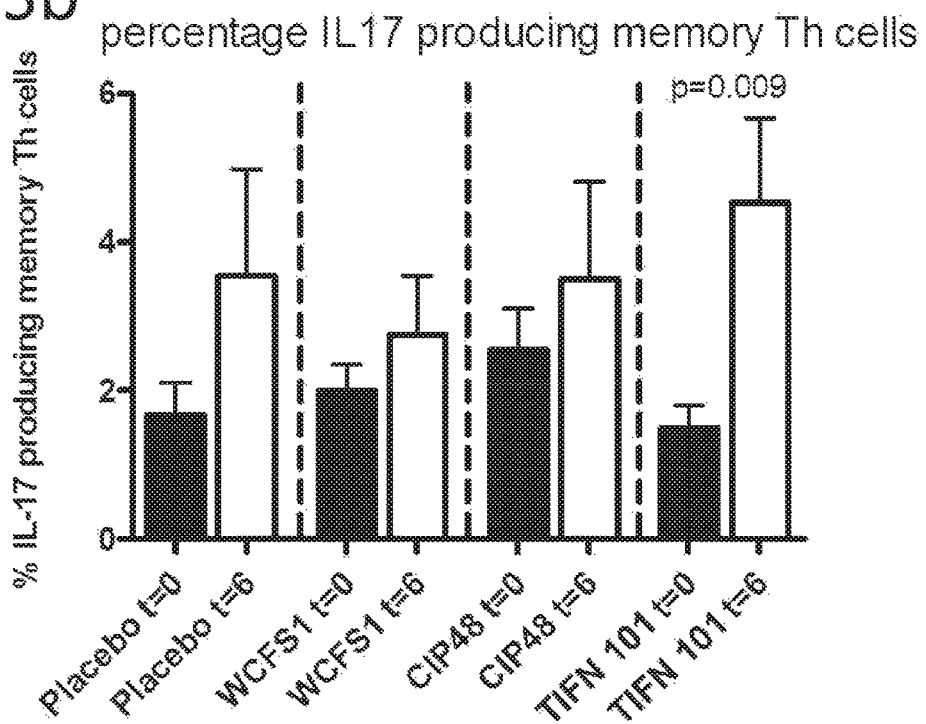
Figure 3C:
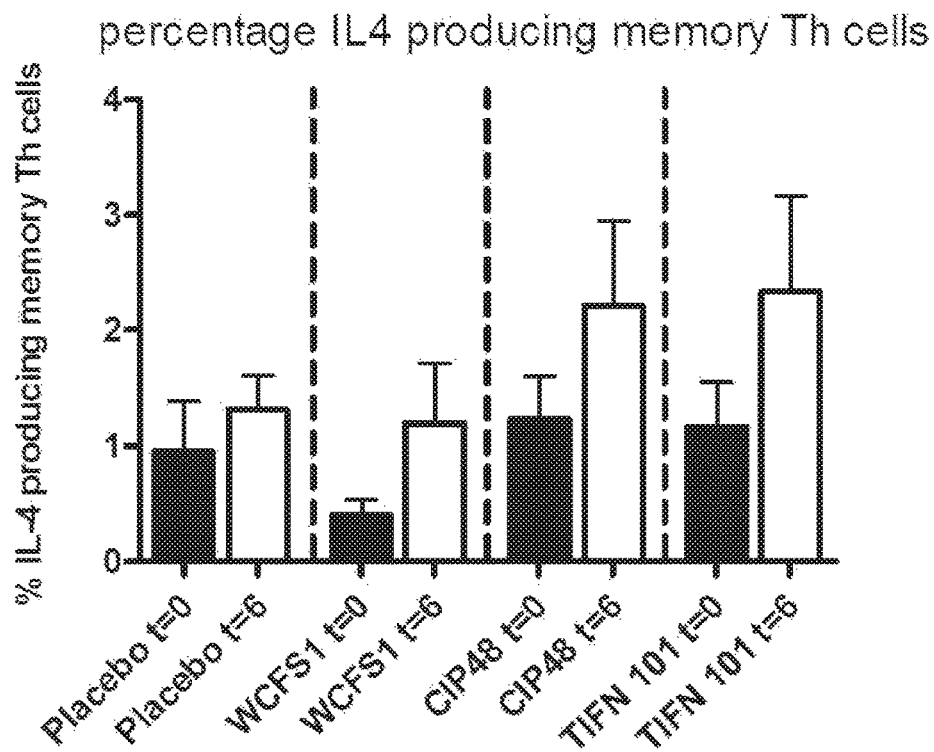
Figure 3D:
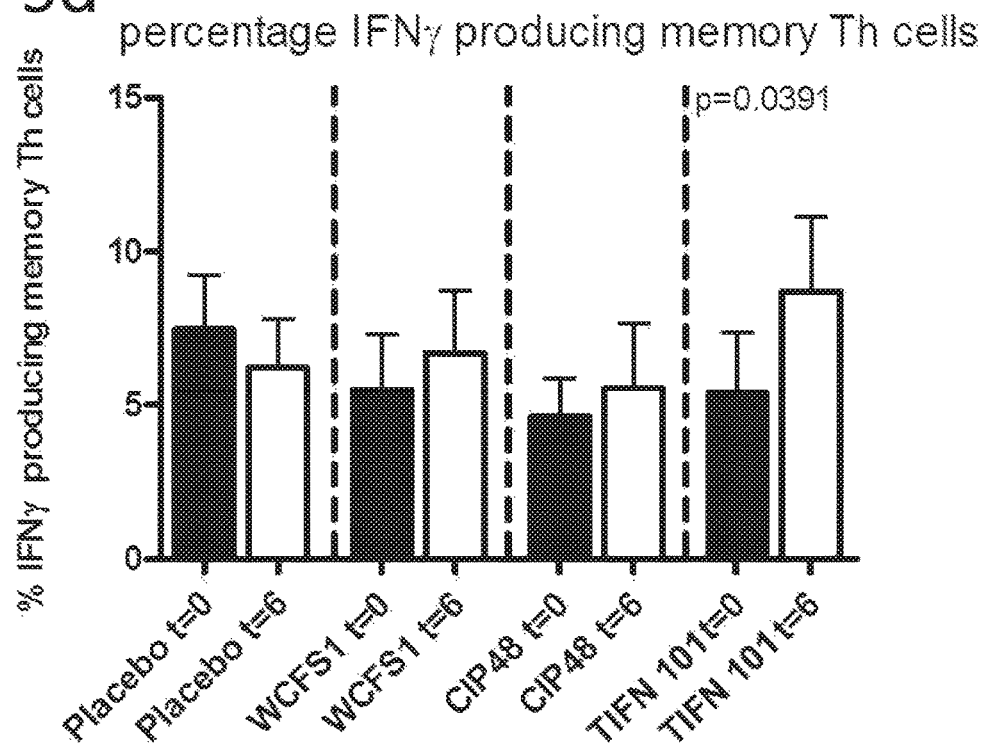

(FIG. 2b). Moreover the percentage of IFNγ producing activated memory Th cells was also increased after TIFN 101 treatment (FIG. 2d).

Treatment with L. plantarum strains also affected the cytokine production following a more specific stimulation by TT (FIG. 3a-d). We studied cytokine production of memory Th cells in order to study the effect of L. plantarum treatment on memory T cells. After TIFN 101 treatment, the percentage IL-17 and the percentage IFNγ producing activated memory Th cells were significantly increased (FIGS. 3b and 3d, respectively), while no effects of the other L. plantarum on cytokine production of memory Th after TT stimulation were observed.

Figure 4A:
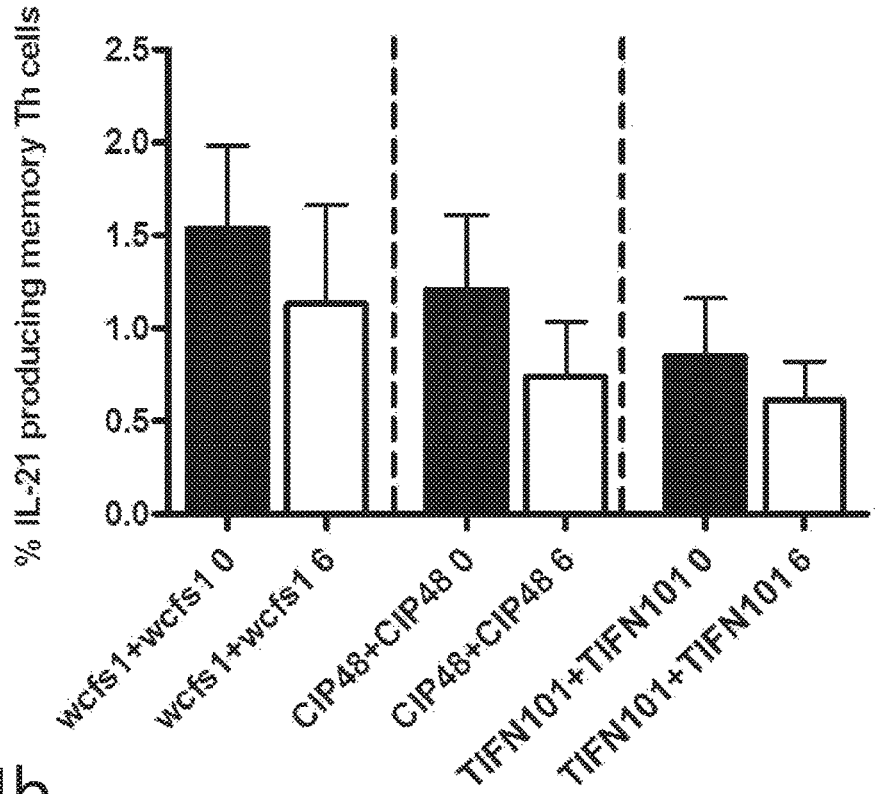
Figure 4B:
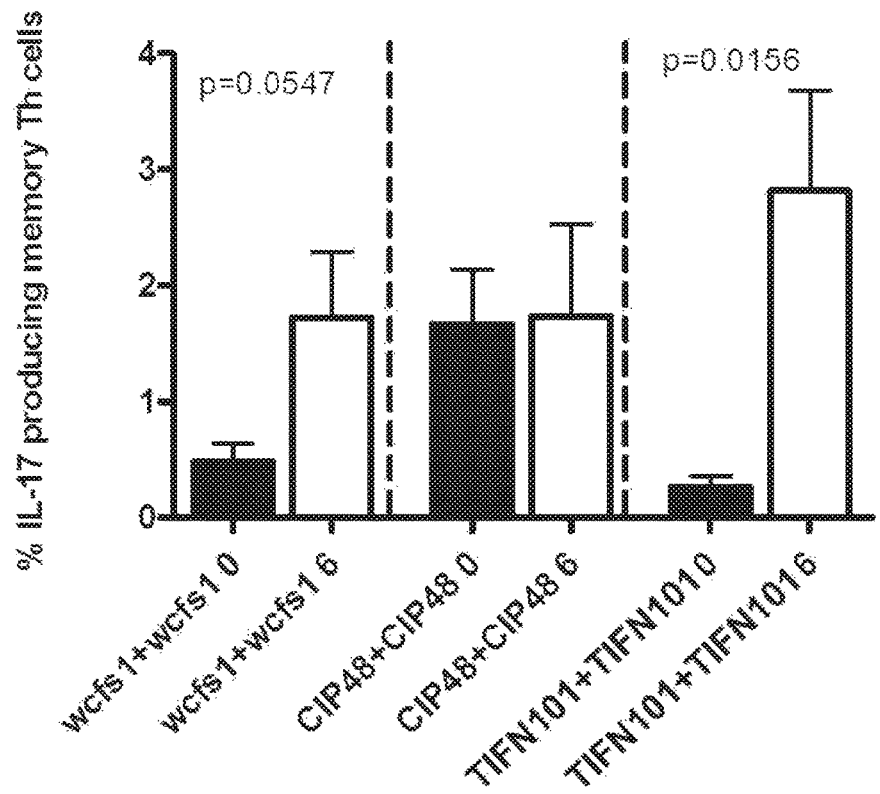
Figure 4C:
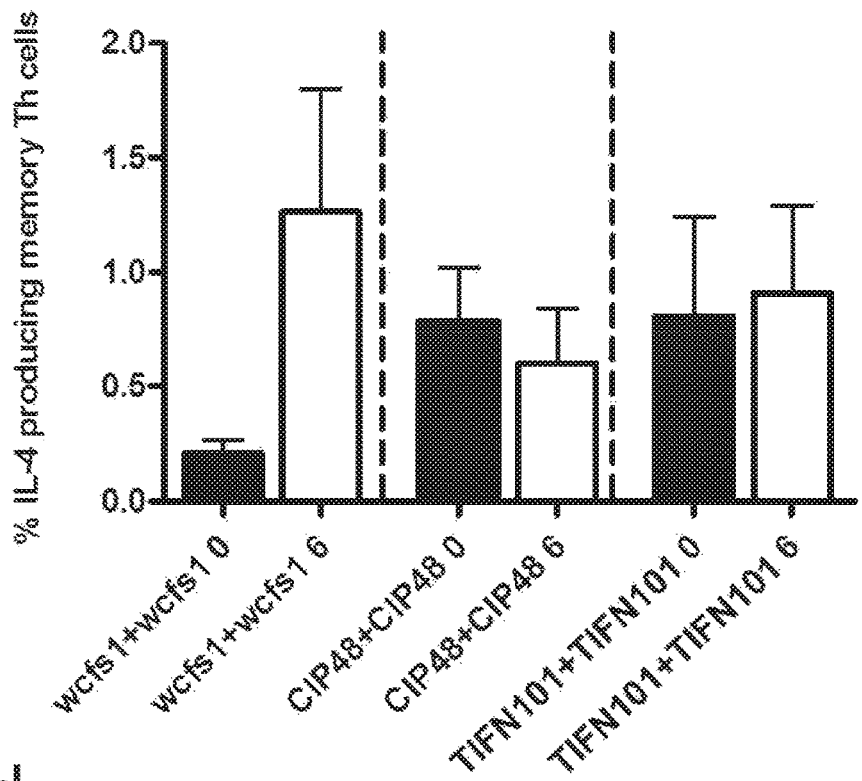
Figure 4D:
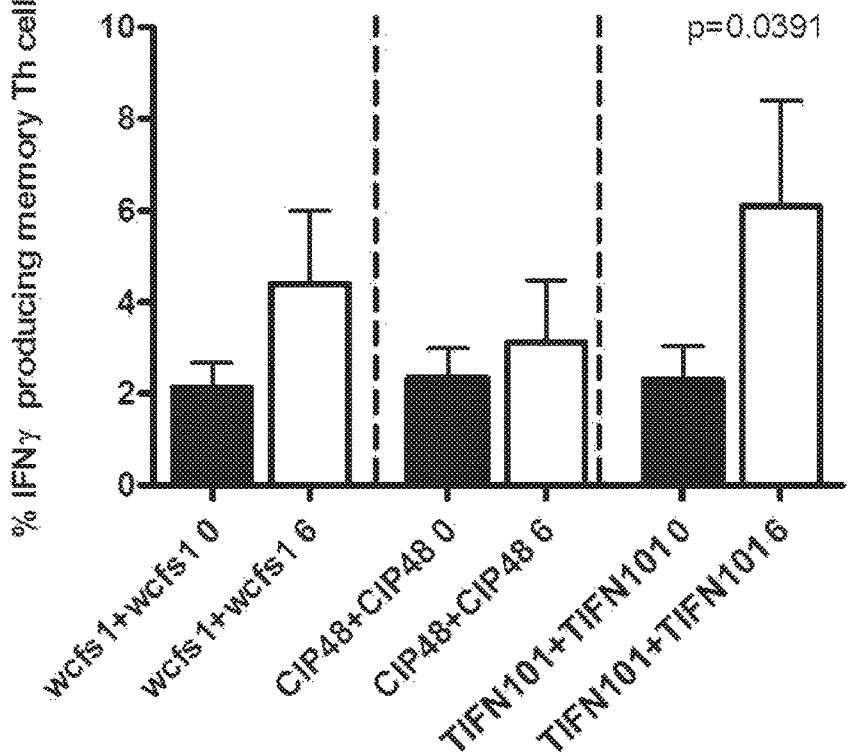

Finally, we stimulated blood samples of the individuals with cell extracts of the L. plantarum strain that they had consumed in the study (FIG. 4a-d). We observed that subjects who were treated with WCFS1, showed an increased IL-17 response after stimulation with WCFS1 cell extracts (FIG. 4b). Other cytokines were not affected by this treatment. There were no differences in cytokine production in subjects when treated with CIP48, when their blood was stimulated with CIP48 cell extract. When subjects were treated with TIFN 101, their activated memory cells showed an increased IL-17 and IFNγ production following stimulation with TIFN 101 cell extract (FIGS. 4b and d, respectively).

Figure 5A:
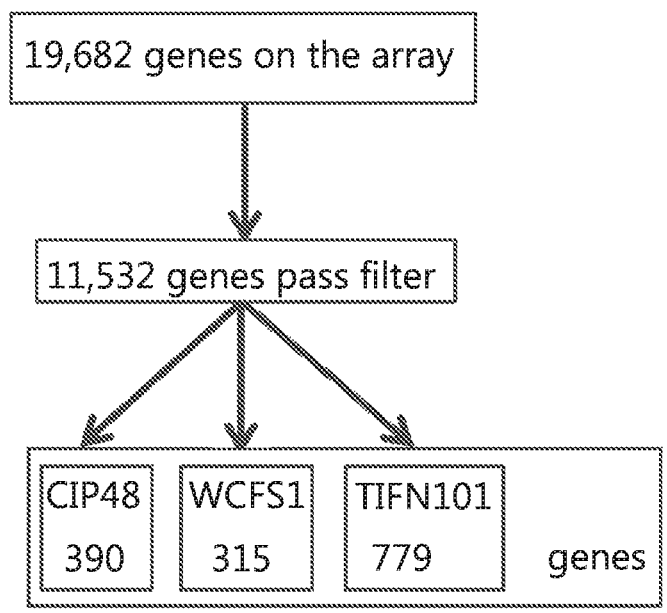
Figure 5B:
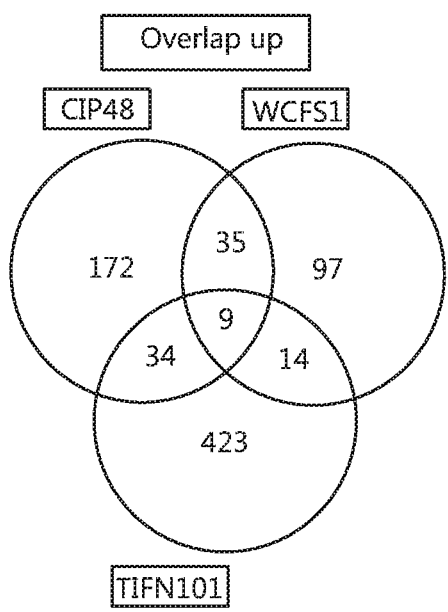
Figure 5C:
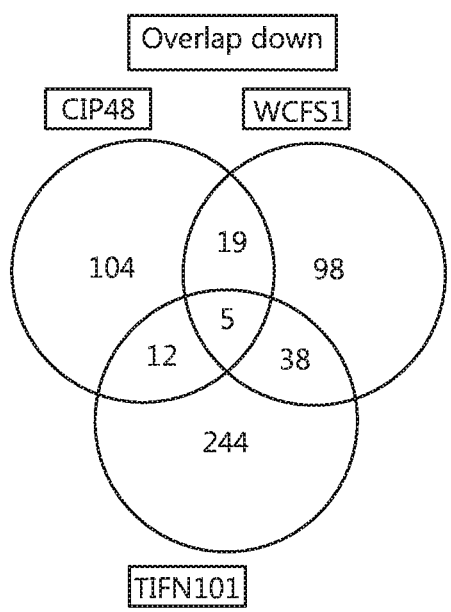

Differential Transcriptional Response in Duodenal Mucosa Upon Exposure to the Three L. plantarum Strains Although, we compared strains and not different species we found very different numbers of genes that were up- or downregulated in the stressed intestine of the subjects exposed to the three L. plantarum strains. After treatment with the three strains, 315 genes were differentially regulated with L. plantarum WCFS1, 390 with CIP48 and as many as 779 with TIFN 101 (FIG. 5a). Of these genes WCFS1 shared only 35 upregulated genes with CIP48 and 9 with TIFN 101 (FIG. 5b). An additional 19 genes were downregulated when CIP48 was compared with WCFS1 and another 5 with TIFN 101 (FIG. 5c). Shared genes were mainly involved in general cellular functions and metabolism. As expected, in an indomethacin-stressed intestine also in placebo treated controls, expression of many genes associated with cellular repair were upregulated.

To gain more insight into the changes induced by the L. plantarum treatment, genes were subsequently ranked according to mean fold-change in expression. Listed are the 10 highest induced and 10 lowest induced genes in Tables 2-3. WCFS1 and CIP48 shared the downregulation of 6 small nucleolar RNAs (snoRNAs), i.e. snoRNA, (H)C/D (ACA) box 6, 14b, 53, 57, 60, 388.

TIFN 101 produced a completely different profile (Table 4). Of the most highly induced genes in TIFN 101, (the most immunological active L. plantarum) 8 of the 10 are related to immunity, these are immunoglobulin lambda variable 6-57, putative V-set and immunoglobulin domain-containing protein 6-like, immunoglobulin lambda variable 7-46, interferon regulatory factor 4, GDNF family, CD27, CD79a, and plasminogen activator.

Based on the immune data we expected to find differential changes by specific transcription factors. To identify these transcription factors and to identify pathways regulated by the different strains, we performed Ingenuity Pathway Analysis (IPA). IPA uses information from literature combined with gene expression changes to predict a role of transcription factors in the dataset. TIFN 101 induced more changed than CIP48 and WCSF1 in the NSAID-stressed intestine. The most significant set of target genes in the TIFN 101 group were immunology related genes. TIFN 101 upregulated MHC-II α while with CIP48 and WCFS1 we found a downregulation of MHC-II β. This might explain the enhanced responses to antigens such as TT in the TIFN 101 treated group. Another pathway that might contribute to the enhanced responses in TIFN 101 is the upregulation of genes involved in leucocyte extravasation. An interesting observation is that TIFN 101 enhances RAPL which is a GTPase involved in regulating integrin affinity and enhancing the adhesion of leucocytes. Concomitantly an upregulation of essential adhesion molecules such as ICAM-1 and Cadherin 5 (CDH-5) was upregulated illustrating the upregulation of immune cell migration pathways by TIFN 101. Also with CIP48 and WCFS1 some regulation of leukocyte extravasation was observed but this was much less pronounced than for the TIFN 101 group.

Differential Gene Expression Profiles Between the Three L. plantarum Strains

Due to the differential effects of the three L. plantarum strains, L. plantarum CIP104448, and L. plantarum TIFN 101 were sequenced, annotated and compared with the genome (chromosome and plasmids) of L. plantarum WCFS1 (Siezen et al., 2012). A total of 3010 ortholog groups (OGs) were assigned to the chromosome based on this ordering of contigs to the template WCFS1 genome. The three genomes shared 2455 of the 3010 chromosomal OGs (=81.5%), which is defined as the core genome for this study. Unique genes in TIFN 101 are listed in Table 5. When the contigs and OGs/genes are included that do not match to the WCFS1 chromosome much higher numbers of unique genes are found for the CIP48 and TIFN 101 genomes. Many of the unique genes in TIFN 101 are on plasmids (see Table 5). The analysis e.g. revealed that L. plantarum CIP104448 lacks the complete plantaricin biosynthesis gene cluster (and a large set of genes adjacent to this cluster (i.e. OGs 334-348), and the entire gene cluster for EPS biosynthesis. L. plantarum TIFN 101 is missing some genes associated with plantaricin biosynthesis as well as genes for exopolysaccharide biosynthesis, many sugar utilization cassettes, and two large LPXTG-anchored mucus-binding proteins.

TABLE 2

The ten most up-and down-regulated genes in NSAID-stressed human intestine after consumption of L. plantarum WCFS1 (WCSF1).

| | Gene name | IBMT p value | Mean fold versus control |
|---|---|---|---|
| Top 10: Upregulated genes placebo versus WCFS1 | | | |
| kinesin family member 20B | KIF20B | 0.01 | 1.34 |
| microRNA 186 | MIR186 | 0.03 | 1.31 |
| guanylate cyclase activator 2A (guanylin) | GUCA2A | 0.04 | 1.31 |
| integrin, alpha 4 (antigen CD49D, alpha 4 subunit of VLA-4 receptor) | ITGA4 | 0.01 | 1.31 |
| centromere protein E, 312 kDa | CENPE | 0.05 | 1.30 |
| putative homeodomain transcription factor 1 | PHTF1 | 0.00 | 1.30 |
| spindle and kinetochore associated complex subunit 2 | SKA2 | 0.01 | 1.29 |
| killer cell lectin-like receptor subfamily D, member 1 | KLRD1 | 0.00 | 1.29 |

TABLE 2-continued

The ten most up-and down-regulated genes in NSAID-stressed human intestine after consumption of *L. plantarum* WCFS1 (WCSF1).

| Gene name | Gene name | IBMT p value | Mean fold versus control |
|---|---|---|---|
| gamma-aminobutyric acid (GABA) A receptor, alpha 2 | GABRA2 | 0.02 | 1.27 |
| retinitis pigmentosa GTPase regulator | RPGR | 0.01 | 1.27 |
| Top 10: Downregulated genes placebo versus WCFS1 | | | |
| small nucleolar RNA, H/ACA box 16A | SNORA16A | 0.02 | −1.35 |
| small nucleolar RNA, C/D box 53 | SNORD53 | 0.04 | −1.36 |
| contactin 3 (plasmacytoma associated) | CNTN3 | 0.00 | −1.38 |
| small nucleolar RNA, C/D box 6 | SNORD6 | 0.04 | −1.39 |
| small nucleolar RNA, H/ACA box 57 | SNORA57 | 0.00 | −1.44 |
| small nucleolar RNA, H/ACA box 60 | SNORA60 | 0.00 | −1.44 |
| small nucleolar RNA, H/ACA box 14A | SNORA14A | 0.03 | −1.49 |
| small nucleolar RNA, H/ACA box 38B (retrotransposed) | SNORA38B | 0.01 | −1.58 |
| small nucleolar RNA, H/ACA box 14B | SNORA14B | 0.01 | −1.58 |
| small Cajal body-specific RNA 4 | SNORA16A | 0.01 | −1.72 |

TABLE 3

The ten most up-and down-regulated genes in NSAID-stressed human intestine after consumption of *L. plantarum* CIP104448 (CIP48).

| Gene name | Gene name | IBMT p value | Mean fold versus control |
|---|---|---|---|
| Top 10: Upregulated genes placebo versus CIP48 | | | |
| coiled-coil domain containing 59 | CCDC59 | 0.01 | 1.33 |
| aldehyde dehydrogenase 1 family, member L2 | ALDH1L2 | 0.03 | 1.32 |
| KIAA0125 | KIAA0125 | 0.00 | 1.31 |
| phospholipase C, beta 4 | PLCB4 | 0.01 | 1.31 |
| coiled-coil domain containing 102B | CCDC102B | 0.04 | 1.29 |
| RAS guanyl releasing protein 3 (calcium and DAG-regulated) | RASGRP3 | 0.03 | 1.28 |
| peptidase domain containing associated with muscle regeneration 1 | PAMR1 | 0.00 | 1.28 |
| DEP domain containing 1 | DEPDC1 | 0.01 | 1.28 |
| phospholipase A2, group IIA (platelets, synovial fluid) | PLA2G2A | 0.02 | 1.28 |
| heparan sulfate (glucosamine) 3-O-sulfotransferase 3B1 | HS3ST3B1 | 0.04 | 1.28 |
| Top 10: Downregulated genes placebo versus CIP48 | | | |
| potassium channel, subfamily K, member 15 | KCNK15 | 0.05 | −1.33 |
| transient receptor potential cation channel, subfamily V, member 6 | TRPV6 | 0.01 | −1.33 |
| long intergenic non-protein coding RNA 282 | LINC00282 | 0.03 | −1.35 |
| ephrin-A1 | EFNA1 | 0.02 | −1.38 |
| matrix metallopeptidase 10 (stromelysin 2) | MMP10 | 0.05 | −1.41 |

TABLE 3-continued

The ten most up-and down-regulated genes in NSAID-stressed human intestine after consumption of *L. plantarum* CIP104448 (CIP48).

| Gene name | Gene name | IBMT p value | Mean fold versus control |
|---|---|---|---|
| angiopoietin-like 4 | ANGPTL4 | 0.03 | −1.47 |
| heme oxygenase (decycling) 1 | HMOX1 | 0.00 | −1.50 |
| nuclear factor, interleukin 3 regulated | NFIL3 | 0.01 | −1.52 |
| major facilitator superfamily domain containing 2A | MFSD2A | 0.02 | −1.59 |
| glucose-6-phosphatase, catalytic subunit | G6PC | 0.02 | −1.65 |

TABLE 4

The ten most up-and down-regulated genes in NSAID-stressed human intestine after consumption of *L. plantarum* TIFN 101

| Gene name | Gene name | IBMT p value | Mean fold versus control |
|---|---|---|---|
| Top 10 Upregulated genes placebo versus TIFN 101 | | | |
| immunoglobulin lambda variable 6-57 | IGLV6-57 | 0.01 | 1.63 |
| putative V-set and immunoglobulin domain-containing protein 6-like | LOC642131 | 0.00 | 1.55 |
| immunoglobulin lambda variable 7-46 (gene/pseudogene) | IGLV7-46 | 0.04 | 1.48 |
| heparan sulfate (glucosamine) 3-O-sulfotransferase 3B1 | HS3ST3B1 | 0.00 | 1.41 |
| interferon regulatory factor 4 | IRF4 | 0.00 | 1.40 |
| GDNF family receptor alpha 2 | GFRA2 | 0.00 | 1.40 |
| CD27 molecule | CD27 | 0.01 | 1.40 |
| CD79a molecule, immunoglobulin-associated alpha | CD79A | 0.03 | 1.38 |
| plasminogen activator, tissue | PLAT | 0.00 | 1.37 |
| Den-like domain family, member 3 | DERL3 | 0.00 | 1.37 |
| Top 10: Downregulated genes placebo versus TIFN 101 | | | |
| small nucleolar RNA, H/ACA box 38B (retrotransposed) | SNORA38B | 0.04 | −1.40 |
| small nucleolar RNA, H/ACA box 21 | SNORA21 | 0.03 | −1.40 |
| small nucleolar RNA, H/ACA box 60 | SNORA60 | 0.01 | −1.41 |
| small nucleolar RNA, C/D box 53 | SNORD53 | 0.01 | −1.43 |
| ephrin-A1 | EFNA1 | 0.00 | −1.45 |
| small nucleolar RNA, C/D box 6 | SNORD6 | 0.02 | −1.46 |
| small nucleolar RNA, H/ACA box 57 | SNORA57 | 0.00 | −1.47 |
| small nucleolar RNA, H/ACA box 14B | SNORA14B | 0.00 | −1.73 |
| family with sequence similarity 5, member C | FAM5C | 0.03 | −1.97 |
| small Cajal body-specific RNA 4 | SCARNA4 | 0.00 | −2.00 |

TABLE 5

Summary of main unique contigs/gene clusters/genes in L. plantarum TIFN 101; the sequence identity numbers are depicted in column 3, the first SEQ ID NO depicts the polynucleotide sequence, the second SEQ ID NO depicts the encoded polypeptide [polynucleotide polypeptide].

| OGs | Contains functions | SEQ ID NO: |
|---|---|---|
| chromosome | | |
| 185 | MFS family transporter | 176; 260 |
| 186 | fumarate reductase/succinate dehydrogenase flavoprotein | 177; 261 |
| 187 | Transcriptional regulator, AraC family | 178; 262 |
| 382 | toxin-antitoxin system, antitoxin component MazE, AbrB family | 179; 263 |
| 383 | toxin-antitoxin system, toxin component MazF, PemK family | 180; 264 |
| 409 | Hypothetical protein | 181; 265 |
| 410 | Conserved ankyrin repeat protein, putative | 182; 266 |
| 411 | integral membrane protein | 183; 267 |
| 461 | nitrate/sulfonate/bicarbonate ABC transporter, substrate-binding protein | 184; 268 |
| 462 | nitrate/sulfonate/bicarbonate ABC transporter, permease protein | 185; 269 |
| 463 | nitrate/sulfonate/bicarbonate ABC transporter, ATP-binding protein | 186; 270 |
| 1197 | ADP-ribosylglycohydrolase | 187; 271 |
| 1986 | abortive infection bacteriophage resistance protein | 188; 272 |
| 2366 | cell wall hydrolase, glycosyl hydrolase family 25 | 189; 273 |
| 2549 | membrane proteinase PrsW, regulator of anti-sigma factor | 190; 274 |
| 2583 | hypothetical membrane protein, YfhO family | 191; 275 |
| 2610 | Fructokinase (EC 2.7.1.4) | 192; 276 |
| 2611 | glycosyl hydrolase, family 38 | 193; 277 |
| 2612 | PTS system, IIC component | 194; 278 |
| 2613 | PTS system, fructose-specific IIBC component (EC 2.7.1.69) | 195; 279 |
| 2614 | (EC 2.7.1.69)/PTS system, fructose-specific IIC component (EC 2.7.1.69) | 196; 280 |
| 2615 | Transcription antiterminator, BglG family | 197; 281 |
| on putative plasmids | | |
| 3299 | hydrolase, HD superfamily, C-terminus | 198; 282 |
| 3300 | Ribonucleotide reduction protein NrdI | 199; 283 |
| 3301 | Ribonucleotide reductase of class Ib (aerobic), alpha subunit (EC 1.17.4.1) | 200; 284 |
| 3302 | Ribonucleotide reductase of class Ib (aerobic), beta subunit (EC 1.17.4.1) | 201; 285 |
| 3303 | Ribonucleotide reductase of class Ib (aerobic), beta subunit (EC 1.17.4.1) | 202; 286 |
| 3304 | transposase, fragment | 203; 287 |
| 3305 | Site-specific recombinase, DNA invertase Pin related protein | 204; 288 |
| 3306 | membrane protein with DUF161 and DUF2179 domains, YitT family | 205; 289 |
| 3307 | Na(+)/H(+) antiporter | 206; 290 |
| 3308 | Voltage-gated chloride channel family protein | 207; 291 |
| 3323 | Glucose uptake protein | 208; 292 |
| 3324 | Mannose-6-phosphate isomerase | 209; 293 |
| 3325 | hypothetical protein, C-terminus | 210; 294 |
| 3326 | hypothetical protein | 211; 295 |
| 3327 | Glutamine synthetase type I (EC 6.3.1.2) | 212; 296 |
| 3328 | transposase | 213; 297 |
| 3329 | toxin-antitoxin system, toxin component, PemK/MazF family | 214; 298 |
| 3330 | toxin-antitoxin system, antitoxin component, PemI/MazE family | 215; 299 |
| 3331 | integrase/recombinase | 216; 300 |
| 3332 | hypothetical protein, C-terminus | 217; 301 |
| 3333 | hypothetical protein | 218; 302 |
| 3334 | Cold shock protein CspA | 219; 303 |
| 3335 | toxin-antitoxin system, RelE/StbE family; replication protein RepA | 220; 304 |
| 3336 | hypothetical protein | 221; 305 |
| 3337 | Transcriptional regulator, PBSX/Xre family | 222; 306 |

TABLE 5-continued

Summary of main unique contigs/gene clusters/genes in *L. plantarum* TIFN 101; the sequence identity numbers are depicted in column 3, the first SEQ ID NO depicts the polynucleotide sequence, the second SEQ ID NO depicts the encoded polypeptide [polynucleotide polypeptide].

| OGs | Contains functions | SEQ ID NO: |
|---|---|---|
| 3338 | hypothetical protein | 223; 307 |
| 3339 | integrase/recombinase | 224; 308 |
| 3340 | toxin-antitoxin system, antitoxin component, Phd_YefM family | 225; 309 |
| 3341 | toxin-antitoxin system, toxin component, RelE/StbE family | 226; 310 |
| 3342 | hypothetical protein | 227; 311 |
| 3343 | hypothetical protein | 228; 312 |
| 3344 | ISEf1, transposase | 229; 313 |
| 3345 | hypothetical membrane protein | 230; 314 |
| 3346 | hypothetical protein, N-terminus | 231; 315 |
| 3347 | replication protein RepA | 232; 316 |
| 3348 | hypothetical protein | 233; 317 |
| 3349 | Transposase IS66 | 234; 318 |
| 3350 | Transposase IS66, N-terminus | 235; 319 |
| 3351 | Transposase IS66, C-terminus | 236; 320 |
| 3352 | Pyridine nucleotide-disulfide oxidoreductase | 237; 321 |
| 3353 | LtrC-like protein | 238; 322 |
| 3354 | Major facilitator: Oxalate: Formate Antiporter | 239; 323 |
| 3355 | transposase IS3/IS911 family protein | 240; 324 |
| 3356 | Excinuclease ABC subunit A paralog | 241; 325 |
| 3357 | site-specific recombinase | 242; 326 |
| 3358 | Iron-sulfur cluster assembly protein SufB, permease, C-terminus | 243; 327 |
| 3359 | membrane protein, MarC family | 244; 328 |
| 3360 | peptidase E | 245; 329 |
| 3361 | hypothetical protein | 246; 330 |
| 3362 | FIG00742910: hypothetical protein | 247; 331 |
| 3363 | alkaline shock protein, Asp23 family | 248; 332 |
| 3364 | hypothetical membrane protein | 249; 333 |
| 3365 | hypothetical protein | 250; 334 |
| 3366-3371 | FIG00753329: hypothetical protein, N-terminus | 251; 335 |
| 3367 | FIG00742586: hypothetical protein | 252; 336 |
| 3368 | replication initiator protein, C-terminus | 253; 337 |
| 3369 | replication initiator protein, N-terminus | 254; 338 |
| 3370 | hypothetical protein | 255; 339 |
| 3371 | plasmid partitioning ATPase ParA | 256; 340 |

Discussion

This study was undertaken to investigate whether *L. plantarum* strains selected in vitro for their differential immune stimulating capacity have different impact on local and systemic immunity in healthy individuals undergoing a mild, commonly encountered stressor of intestinal immunity. All three strains had an effect on immunity but that this effect was highly strain dependent and may not be beneficial in certain contexts. On the basis of results obtained by dendritic cell stimulation with *L. plantarum* strains in vitro the immune properties, of strain. WCFS1 was considered to be proinflammatory, *L. plantarum* CIP104448 as neutral and *L. plantarum* TIFN 101 as regulatory. However, the immune responses to these strains in vivo was very different to that predicted in vitro.

Consumption of NSAID induced reduction in CD4+/ Foxp3 regulatory cells but was prevented by WCFS1 and TIFN 101 administration which should be considered to be a beneficial regulatory effect. CIP48 did not prevent NSAID induced reduction of CD4+Foxp3 T cells and had more negative effects. CIP48 reduced the number of memory cells suggesting a proinflammatory, worsening effect of consumption of this bacterium.

T-cell polarization was studied after different stimuli to gain insight into the mechanisms by which bacteria might influence immunity. A hypothesis we had was that bacterial wall components might induce immune responses (Smelt et al., 2012) and enhance systemic immunity as bystander effect. However, this hypothesis had to be rejected as the sole responsible mechanism as only WCFS1 showed a trend of elevation of IL17 production after challenging whole blood of the WCSF1 consumers with the bacterial strain. The most pronounced stimulator of immunity, i.e. TIFN 101, showed no response to the bacterial extract but enhanced the responses against specific pathogenic antigens such as SEB and that against TT.

The analysis of the mucosal transcriptome suggested that the enhanced memory response is related to TIFN 101 enhanced upregulation of processes associated with T- and B-cell function and antigen presentation. TIFN 101 in contrast to the other bacteria had a pronounced effect on immunological related pathways in the mucosa of the consumers. In particular TIFN 101 enhanced pathways and genes related to antigen presentation. TIFN 101 had a pronounced effect on CD27 upregulation which is required for generation and long-term maintenance of T cell immunity (Huang et al., 2013). Also TIFN 101 enhanced the expression of MHC-II α in mucosa and of key regulatory molecules such as RAPL. RAPL enhances integrin affinity and the adhesion of T-cells (Raab et al., 2010; Zhang and Wang, 2012). These observations in the mucosa may explain the enhanced memory T-cell responses observed in the TIFN 101 consumers. Also B-cell immunity in the mucosa was enhanced as illustrated by upregulation of immunoglobulin regulatory genes and by CD79a. CD79A is also known as B-cell antigen receptor complex-associated protein alpha chain forming together with CD79b protein the B-cell antigen receptor (Herren and Burrows, 2002). CIP48 and WCFS1 did not have these effects or downregulated processes such as antigen presentation in the mucosa.

The observation that bacteria can downregulate snoRNAs in the intestine has to our best knowledge not been reported before. SnoRNA are metabolically stable noncoding RNAs that associate with a set of proteins to form small nucleolar RNPs (snoRNPs). The majority of snoRNA function as guide RNAs in the post-transcriptional synthesis of 2'-O-methylated nucleotides and pseudouridines in rRNAs, small nuclear RNAs (snRNAs) and other cellular RNAs, including mRNAs (Bratkovic and Rogelj, 2011; Esteller, 2011; Williams and Farzaneh, 2012). The relative reduction in snoRNA 53, 57, 60 by CIP48 and WCFS1 suggest a downregulation of methylation of ribosomal RNA (Kiss-Laszlo et al., 1996) and downregulation of 14b diminished pseudouridinilation of RNA (Kiss et al., 2004). Usually this suggest a destabilization of cellular processes (Su et al., 2014), again suggesting that CIP48 and WCFS1 are not beneficial for a mildly stressed intestinal environment.

We applied genome sequencing of *L. plantarum* CIP104448 and *L. plantarum* TIFN 101 to identify possible gene clusters that might be responsible for the differential biological effects of the three *L. plantarum* strains. Several hundred novel *L. plantarum* genes were found in strain CIP48 (340 new OGs) and TIFN 101 (177 OGs) compared to strain WCFS1. Only a small number of these (47 OGs) are shared by both CIP48 and TIFN 101. The majority of these novel genes appear to be on plasmids. *L. plantarum* TIFN 101 partly lacks the plantaricin biosynthesis clusters. These genes have in previous studies been linked to strain differences in cytokine production (Meijerink et al., 2010; Wells et al., 2011) but were shown here not to be associated with immune effects in vivo. Also *L. plantarum* CIP104448 and *L. plantarum* TIFN 101 lack very large regions of the sugar metabolism. These adaptations have been attributed to adaptations to environmental factors which are interesting targets to identify genes associated with probiotic effects (Molenaar et al., 2005). Not only presence but also absence of genes may enhance immune effects of bacteria (Smelt et al., 2013b). This comparative genomics study in which effects of *L. plantarum* supplementation on the mucosal transcriptome were combined with systemic immune activation parameters provides many leads for follow-up experimental work to identify genes that are responsible for or involved in the observed differences in immune effects in the human subject.

REFERENCE LIST

Belkaid Y, Hand T W. Role of the microbiota in immunity and inflammation. Cell 2014; 157:121-41. doi: 10.1016/j.cell.2014.03.011.

Cao S, Feehley T J, Nagler C R. The role of commensal bacteria in the regulation of sensitization to food allergens. FEBS Lett 2014; 1:00312-3.

de Kivit S, Tobin M C, Forsyth C B, Keshavarzian A, Landay A L. Regulation of Intestinal Immune Responses through TLR Activation: Implications for Pro- and Prebiotics. Front Immunol 2014; 5:60. eCollection 2014.

Geuking M B, Koller Y, Rupp S, McCoy K D. The interplay between the gut microbiota and the immune system. Gut Microbes 2014; 5:3.

Walker M M, Talley N J. Review article: bacteria and pathogenesis of disease in the upper gastrointestinal tract—beyond the era of *Helicobacter pylori*. Aliment Pharmacol Ther 2014; 39:767-79. doi: 10.1111/apt.12666. Epub 2014 Feb. 24.

Meijerink M, van H S, Taverne N, Wels M, de V P, Bron P A, et al. Identification of genetic loci in *Lactobacilli plantarum* that modulate the immune response of dendritic cells using comparative genome hybridization. PLoSOne 2010; 5:e10632.

Meijerink M, Wells J M, Taverne N, de Zeeuw Brouwer M L, Hilhorst B, Venema K, et al Immunomodulatory effects of potential probiotics in a mouse peanut sensitization model. FEMS Immunol Med Microbiol 2012; 65:488-96.

Wells J M, Rossi O, Meijerink M, van B P. Epithelial crosstalk at the microbiota-mucosal interface. Proc Natl Acad Sci USA 2011; 108 Suppl 1:4607-14.

van Baarlen P, Troost F, van der Meer C, Hooiveld G, Boekschoten M, Brummer R J, et al. Human mucosal in vivo transcriptome responses to three *lactobacilli* indicate how probiotics may modulate human cellular pathways. Proc Natl Acad Sci USA 2011; 108:4562-9. doi: 10.1073/pnas.1000079107. Epub 2010 Sep. 7.

van Baarlen P, Troost F J, van Hemert S, van der Meer C, de Vos W M, de Groot P J, et al. Differential NF-kappaB pathways induction by *Lactobacilli plantarum* in the duodenum of healthy humans correlating with immune tolerance. Proc Natl Acad Sci USA 2009; 106:2371-6. doi: 10.1073/pnas.0809919106. Epub 2009 Feb. 3.

van Hemert S, Meijerink M, Molenaar D, Bron P A, de Vos P, Kleerebezem M, Wells J M, Marco M L Identification of *Lactobacilli plantarum* genes modulating the cytokine response of human peripheral blood mononuclear cells BMC microbiology 2010, 10 (1) 293

Smelt M J, de Haan B J, Bron P A, van Swam I, Meijerink M, Wells J M, et al. The Impact of *Lactobacilli plantarum* WCFS1 Teichoic Acid D-Alanylation on the Generation of Effector and Regulatory T-cells in Healthy Mice. PLoS One 2013; 8:e63099.

Smelt M J, de Haan B J, Bron P A, van Swam I, Meijerink M, Wells J M, et al. *L. plantarum, L. salivarius*, and *L. lactis* attenuate Th2 responses and increase Treg frequencies in healthy mice in a strain dependent manner PLoS One 2012; 7:e47244.

Schoultz I, McKay C M, Graepel R, Phan V C, Wang A, Soderholm J, et al. Indomethacin-induced translocation of bacteria across enteric epithelia is reactive oxygen species-dependent and reduced by vitamin C. Am J Physiol Gastrointest Liver Physiol 2012; 303:G536-45. doi: 10.1152/ajpgi.00125.2012. Epub 2012 Jun. 14.

Deasy A, Read R C. Challenges for development of meningococcal vaccines in infants and children. Expert Rev Vaccines 2011; 10:335-43. doi: 10.1586/erv.11.3. (16)

Edwards K M, Berbers G A. Immune responses to pertussis vaccines and disease. J Infect Dis 2014; 209:S10-5. doi: 1093/infdis/jit560. Epub 2013 Oct. 31.

Kerneis S, Launay O, Turbelin C, Batteux F, Hanslik T, Boelle P Y. Long-term immune responses to vaccination in HIV-infected patients: a systematic review and meta-analysis. Clin Infect Dis 2014; 58:1130-9. doi: 10.093/cid/cit937. Epub 2014 Jan. 10.

Poorolajal J, Mahmoodi M, Haghdoost A, Majdzadeh R, Nasseri-Moghaddam S, Ghalichi L, et al. Booster dose vaccination for preventing hepatitis B. Cochrane Database Syst Rev 2010: CD008256. doi: 10.1002/14651858.CD008256.pub2.

Schure R M, Hendrikx L H, de Rond L G, Ozturk K, Sanders E A, Berbers G A, et al. T-cell responses before and after the fifth consecutive acellular pertussis vaccination in 4-year-old Dutch children. Clin Vaccine Immunol 2012; 19:1879-86. doi: 10.128/CVI.00277-12. Epub 2012 Sep. 26.

Marco, M. L., S. Pavan, and M. Kleerebezem, *Towards understanding molecular modes of probiotic action.* Curr Opin Biotechnol, 2006. 17(2): p. 204-10.

Corr, S. C., C. Hill, and C. G. Gahan, *Understanding the mechanisms by which probiotics inhibit gastrointestinal pathogens.* Adv Food Nutr Res, 2009. 56: p. 1-15.

Saulnier, D. M. A., et al., *Mechanisms of probiosis and probiosis: considerations for enhanced functional foods.* Current Opinion in Biotechnology, 2009. 20(2): p. 135-141.

Saxelin, M., et al., *Probiotic and other functional microbes: from markets to mechanisms.* Curr Opin Biotechnol, 2005. 16(2): p. 204-11.

Ma, D., P. Forsythe, and J. Bienenstock, *Live Lactobacillus reuteri is essential for the inhibitory effect on tumor necrosis factor alpha-induced interleukin-8 expression.* Infect Immun, 2004. 72(9): p. 5308-14.

Gobbetti, M., R. D. Cagno, and M. De Angelis, *Functional microorganisms for functional food quality.* Crit Rev Food Sci Nutr, 2010. 50(8): p. 716-27.

Smyth et al. 2004, Stat Appl Genet Mol Biol

Subramanian et al 2005, Proc Natl Acad Sci USA PMID 16199517

Tarazona, R., J. G. Casado, O. Delarosa, J. Torre-Cisneros, J. L. Villanueva, B. Sanchez, M. D. Galiani, R. Gonzalez, R. Solana, and J. Pena. 2002. Selective depletion of CD56(dim) NK cell subsets and maintenance of CD56 (bright) NK cells in treatment-naive HIV-1-seropositive individuals. *J Clin Immunol* 22:176-183.

Jacobs, R., G. Hintzen, A. Kemper, K. Beul, S. Kempf, G. Behrens, K. W. Sykora, and R. E. Schmidt. 2001. CD56bright cells differ in their KIR repertoire and cytotoxic features from CD56dim NK cells. *Eur J Immunol* 31:3121-3127.

Siezen, R. J., C. Francke, B. Renckens, J. Boekhorst, M. Wels, M. Kleerebezem, and S. A. van Hijum. 2012. Complete resequencing and reannotation of the *Lactobacillus plantarum* WCFS1 genome. *J Bacteriol* 194:195-196.

Huang, J., C. Jochems, A. M. Anderson, T. Talaie, A. Jales, R. A. Madan, J. W. Hodge, K. Y. Tsang, D. J. Liewehr, S. M. Steinberg, J. L. Gulley, and J. Schlom. 2013. Soluble CD27-pool in humans may contribute to T cell activation and tumor immunity. *J Immunol* 190:6250-6258

Raab, M., H. Wang, Y. Lu, X. Smith, Z. Wu, K. Strebhardt, J. E. Ladbury, and C. E. Rudd. 2010. T cell receptor "inside-out" pathway via signaling module SKAP1-RapL regulates T cell motility and interactions in lymph nodes. *Immunity* 32:541-556.

Zhang, Y., and H. Wang. 2012. Integrin signalling and function in immune cells. *Immunology* 135:268-275.

Herren, B., and P. D. Burrows. 2002. B cell-restricted human mb-1 gene: expression, function, and lineage infidelity. *Immunologic research* 26:35-43.

Bratkovic, T., and B. Rogelj. 2011. Biology and applications of small nucleolar RNAs. *Cellular and molecular life sciences: CMLS* 68:3843-3851.

Esteller, M. 2011. Non-coding RNAs in human disease. *Nature reviews. Genetics* 12:861-874.

Williams, G. T., and F. Farzaneh. 2012. Are snoRNAs and snoRNA host genes new players in cancer? *Nature reviews. Cancer* 12:84-88.

Kiss-Laszlo, Z., Y. Henry, J. P. Bachellerie, M. Caizergues-Ferrer, and T. Kiss. 1996. Site-specific ribose methylation of preribosomal RNA: a novel function for small nucleolar RNAs. *Cell* 85:1077-1088.

Kiss, A. M., B. E. Jady, E. Bertrand, and T. Kiss. 2004. Human box H/ACA pseudouridylation guide RNA machinery. *Molecular and cellular biology* 24:5797-5807.

Su, H., T. Xu, S. Ganapathy, M. Shadfan, M. Long, T. H. Huang, I. Thompson, and Z. M. Yuan. 2014. Elevated snoRNA biogenesis is essential in breast cancer. *Oncogene* 33:1348-1358.

Molenaar, D., F. Bringel, F. H. Schuren, W. M. de Vos, R. J. Siezen, and M. Kleerebezem. 2005. Exploring *Lactobacilli plantarum* genome diversity by using microarrays. *J Bacteriol* 187:6119-6127.

Troost, F. J., W. H. Saris, and R. J. Brummer 2003. Recombinant human lactoferrin ingestion attenuates indomethacin-induced enteropathy in vivo in healthy volunteers. Eur J Clin Nutr 57:1579-1585.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10226492B2). An electronic copy of the "Sequence Listing" will also be available from the USPTO upon request and payment of the fee set forth in 37 CFR 1.19(b)(3).

The invention claimed is:

1. A probiotic formulation comprising at least one food-grade substance and at least one probiotic bacterial strain comprising at least one polynucleotide that has at least 95% sequence identity to:
   a polynucleotide sequence selected from the group consisting of SEQ ID NOs: 177, 183, 188, 205, 207, 219, 244, and 248, and/or
   a polynucleotide encoding a polypeptide with a sequence selected from the group consisting of SEQ ID NOs: 261, 267, 272, 289, 291, 303, 328, and 332.

2. A probiotic formulation according to claim 1, comprising at least one further probiotic bacterial strain.

3. A probiotic formulation according to claim 1, wherein the concentration of probiotic bacterial strains ranges from about 10 to about 50 weight percent and/or about 1 E+6 to about 1 E+12 colony forming units/ml of formulation.

4. A probiotic formulation according to claim 1 that is formed as part of a tablet or that is contained within a capsule.

5. A food product, a formulation for food enrichment, a food supplement, a nutraceutical formulation or a pharmaceutical formulation comprising a probiotic formulation according to claim 1.

6. A container with a liquid volume between 0.5 and 50 ml comprising a probiotic formulation according to claim 1.

7. A container with a liquid volume between 0.5 and 1000 ml comprising a food product, a formulation for food enrichment, a food supplement, a nutraceutical formulation or a pharmaceutical formulation according to claim 5.

8. A probiotic formulation comprising at least one food-grade substance and a probiotic bacterial strain *Lactobacillus plantarum* TIFN 101with accession number CBS 138100.

* * * * *